US010201605B2

(12) United States Patent
Tian et al.

(10) Patent No.: US 10,201,605 B2
(45) Date of Patent: *Feb. 12, 2019

(54) GENE-DELETED VARIANT STRAIN OF PORCINE PSEUDORABIES VIRUS, VACCINE COMPOSITION, METHOD OF MAKING THE SAME AND USE THEREOF

(71) Applicant: Pulike Biological Engineering, Inc., Luoyang (CN)

(72) Inventors: Kegong Tian, Luoyang (CN); Xuke Zhang, Luoyang (CN); Jinzhong Sun, Luoyang (CN); Feifei Tan, Luoyang (CN)

(73) Assignee: PULIKE BIOLOGICAL ENGINEERING, INC. (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/213,662

(22) Filed: Jul. 19, 2016

(65) Prior Publication Data

US 2016/0317650 A1    Nov. 3, 2016

Related U.S. Application Data

(63) Continuation of application No. 15/054,404, filed on Feb. 26, 2016, which is a continuation of application
(Continued)

(30) Foreign Application Priority Data

Aug. 22, 2014    (CN) .......................... 2014 1 0418379

(51) Int. Cl.
*A61K 39/00* (2006.01)
*C12N 7/00* (2006.01)
(Continued)

(52) U.S. Cl.
CPC ............ *A61K 39/245* (2013.01); *A61K 39/12* (2013.01); *A61K 45/06* (2013.01); *C12N 7/00* (2013.01);
(Continued)

(58) Field of Classification Search
None
See application file for complete search history.

(56) References Cited

U.S. PATENT DOCUMENTS

| | | | |
|---|---|---|---|
| 5,674,500 A * | 10/1997 | Peeters | A61K 39/245 424/199.1 |
| 6,217,883 B1 * | 4/2001 | Allan | C07K 14/005 424/199.1 |
| 2014/0093535 A1 * | 4/2014 | Wu | A61K 39/12 424/202.1 |

FOREIGN PATENT DOCUMENTS

| | | | |
|---|---|---|---|
| CN | 101489589 A | | 7/2009 |
| CN | 103627678 A | * | 3/2014 |
| CN | 103923884 A | * | 7/2014 |

OTHER PUBLICATIONS

Brideau et al., "The Us9 Gene Product of Pseudorabies Virus, an Alphaherpesvirus, Is a Phosphorylated, Tail-Anchored Type II Membrane Protein," Journal of Virology vol. 72, No. 6: 4560-4570 (1998).*
(Continued)

*Primary Examiner* — Janet L Andres
*Assistant Examiner* — M Franco G Salvoza
(74) *Attorney, Agent, or Firm* — Fish IP Law, LLP

(57) ABSTRACT

The present invention provides an attenuated strain of porcine pseudorabies virus (PRV), in which said attenuated strain of PRV is a variant strain of PRV with inactivation of gI/gE/11K/28K proteins. In addition, the present invention also provides a vaccine composition comprising the attenuated strain of PRV as an antigen, a preparation method and
(Continued)

use thereof. Proved by immunogenicity and pathogenicity testing of the live vaccine, said live PRV vaccine can provide a good protection for pigs with no clinical signs observed, indicating excellent immune protection.

13 Claims, 3 Drawing Sheets

Specification includes a Sequence Listing.

Related U.S. Application Data

No. 14/901,981, filed as application No. PCT/CN2015/070221 on Jan. 6, 2015.

(51) Int. Cl.
  *A61K 39/245* (2006.01)
  *C12N 7/04* (2006.01)
  *A61K 39/12* (2006.01)
  *A61K 45/06* (2006.01)

(52) U.S. Cl.
  CPC ........ *C12N 7/04* (2013.01); *A61K 2039/5252* (2013.01); *A61K 2039/5254* (2013.01); *A61K 2039/543* (2013.01); *A61K 2039/545* (2013.01); *A61K 2039/552* (2013.01); *C12N 2710/16011* (2013.01); *C12N 2710/16634* (2013.01); *C12N 2710/16721* (2013.01); *C12N 2710/16734* (2013.01); *C12N 2710/16762* (2013.01); *C12N 2710/16771* (2013.01); *C12N 2770/20071* (2013.01)

(56) References Cited

OTHER PUBLICATIONS

Lomniczi et al., "Deletions in the Genomes of Pseudorabies Virus Vaccine Strains and Existence of Four Isomers of the Genomes," Journal of Virology, vol. 49, No. 3: 970-979 (1984).*

Wang et al., "A novel gE-deleted pseudorabies virus (PRV) provides rapid and complete protection from lethal challenge with the PRV variant emerging in Bartha-K61-vaccinated swine population in China," Vaccine 32: 3379 (2014).*

Dong et al., "An Overview of Live Attenuated Recombinant Pseudorabies Viruses for Use as Novel Vaccines," Journal of Immunology Research, vol. 2014, Article ID 824630 (2014).*

Maresch et al., "Oral immunization of wild boar and domestic pigs with attenuated live vaccine protects against Pseudorabies virus infection," Veterinary Microbiology 151: 20-25 (2012).*

Bartha, "Experimental reduction of virulence of Aujesky's disease virus," Mag. allator, Lapja, 16: 42-45 (1961).*

Skoda et al., "Immunization against Aujesky's Disease with Live Vaccine," Acta Virol. 8:1-9 (1964).*

Wu et al., "Emergence of virulent pseudorabies virus infection in northern China," J. Vet. Sci 14(3): 363-365 (2013).*

Luo et al., "Pathogenicity and genomic characterization of a pseudorabies virus variant isolated from Bartha-K-61-vaccinated swine population in China," Veterinary Microbiology 174: 107-115 (2014).*

Google English translation of CN 103627678 A (2014).*

Google English translation of CN 103923884 A (2014).*

Chen, Z. et al., "Cloning and sequence analysis of gB, gC, gD genes of pseudorabies virus strain Fa", Fujian Journal of Agricultural Sciences, 2007, vol. 22, No. 2, pp. 120-125.

* cited by examiner

[Fig. 1]
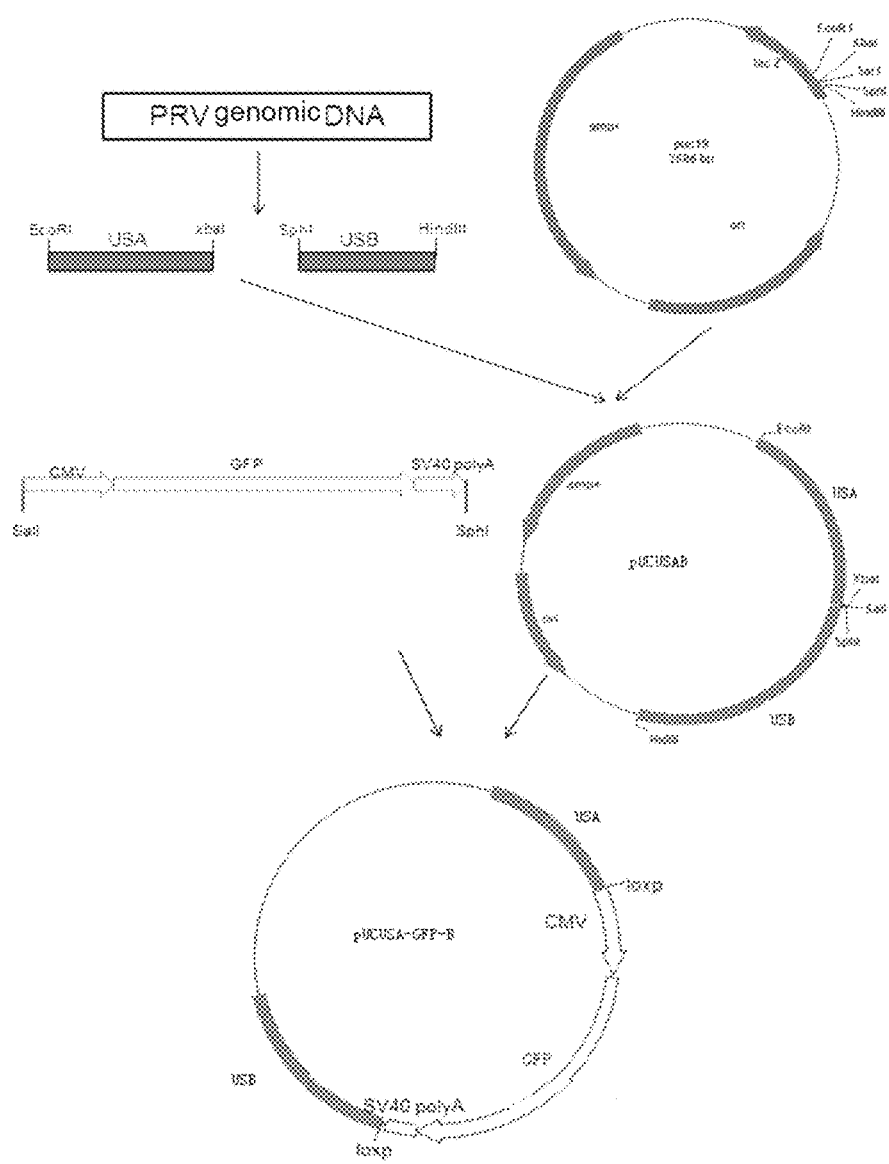

[Fig. 2]
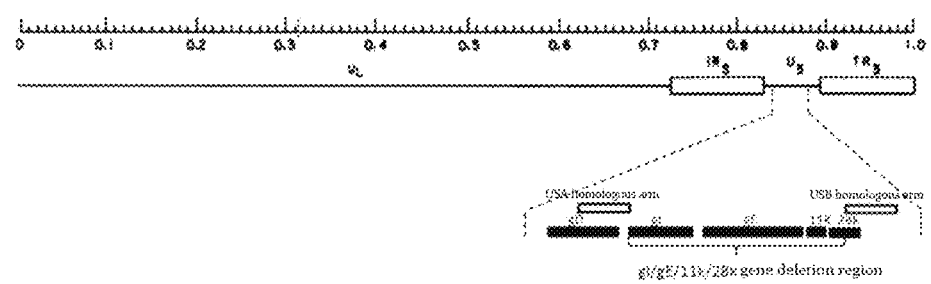
[Fig. 3]
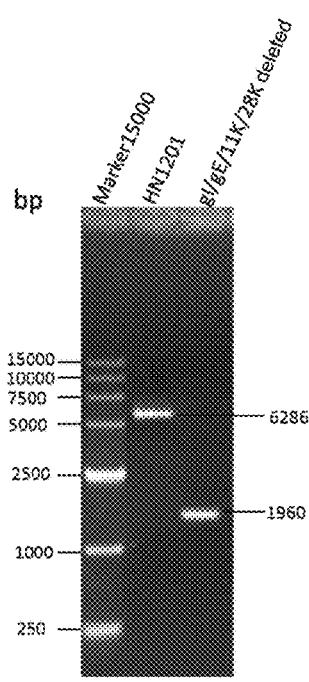

[Fig. 4]
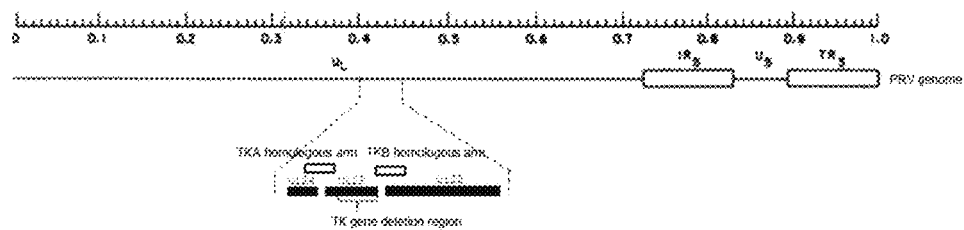
[Fig. 5]
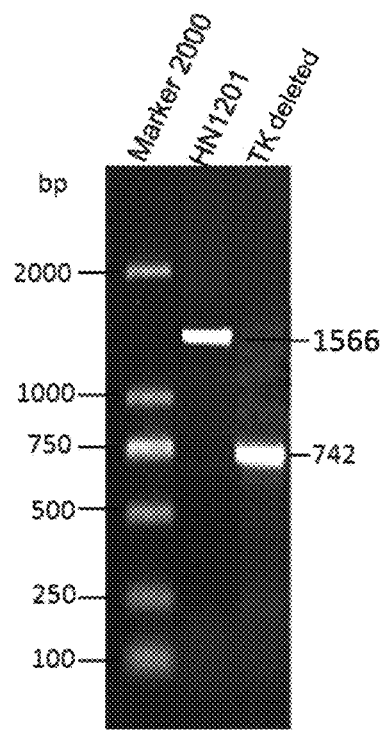

SEQUENCE LISTING

```
<160> NUMBER OF SEQ ID NOS: 21

<210> SEQ ID NO 1
<211> LENGTH: 4320
<212> TYPE: DNA
<213> ORGANISM: PORCINE PSEUDORABIES VIRUS

<400> SEQUENCE: 1
atgatgatgg tggcgcgcga cgtgacccgg ctccccgcgg ggctcctcct cgccgccctg      60
accctggccg ccctgacccc gcgcgtcggg gggcgtcctc ttcaggggcg ccggcgtcag     120
cgtgcacgtc gccggcagcg ccgtcctcgt gcccggcgac gcgcccaacc tgacgataga     180
cgggacgctg ctgtttctgg aggggccctc gccgagcaac tacagcgggc gcgtggagct     240
gctgcgcctc gaccccaagc gcgcctgcta cacgcgcgag tacgccgccg agtacgacct     300 ctgccccgc gtgcaccacg aagccttccg cggctgcctg cgcaagcgcg agccgctcgc     360
ccggcgcgcg tccgccgcgg tggaggcgcg ccggctgctg ttcgtctcgc gcccggcctc     420
gggggacgcg gggtcgtacg tgctgcgggt ccgcgtgaac gggaccacgg acctctttgt     480
gctgacggcc ctggtgccgc cgaggggcg cccgtcccc acgtcgccgc ccgcggacga     540
gtgccggccc gtcgtcggat cgtggcacga cagcctcgcg gtcgtggacc ccgccgagga     600
cgccgtgttc accacccagc ccccgcccga gcccgagccg ccgacgaccc ccgcgccccc     660 ccggggggacc ggcgccaccc ccgagcccg atcggacgag gaggaggagg gtgacgcgga     720
gacgacgacg ccgacgctga ccccggcgcc cgggacccctg gacgcgaacg gcacgatggt     780
```

```
gctgaacgcc agcgtcgtgt cgcgcgtcct gctcgccgcc gccaacgcca cggcgggcgc      840
ccggagcccc gggaagatag ccatggtgct ggggcccacg atcgtcgtcc tcctgatctt      900
cctgggcggg atcgcctgcg tggcccggcg ctgcgcgcgg aatcgcatct accggccgcg      960
acccgggcgg ggatcggcgg tccatgcggc gccccgcgg cgcccgcccc caaccccgtc      1020
gccggggcgc ccgtccccca gcccaagatg acgttggccg agctgcgcca gaagctcgcc      1080
accatcgcag aagaacaata aaaaggtggt gtttgcataa ttttgtgggt ggcgttttat      1140
ctccgtccgc gccgttttaa acctgggcac ccccgcgagt ctcgcacaca ccggggttga      1200
gaccatgcgg cccttctgc tgcgcgccgc gcagctcctg gcgctgctgg ccctggcgct      1260
ctccaccgag gccccgagcc tctccgccga gacgaccccg ggccccgtca ccgaggtccc      1320
gagtccctcg gccgaggtct gggacgacct ctccaccgag gccgacgacg atgacctcaa      1380
cggcgacctc gacggcgacg accgccgcgc gggcttcggc tcggccctcg catccctgag      1440
ggaggcgccc ccggcccatc tggtgaacgt gtccgagggc gccaacttca ccctcgacgc      1500
gcgcggcgac ggcgccgtgc tggccgggat ctggacgttc ctgccgtcc gcggctgcga       1560
cgccgtgtcg gtgaccacgg tgtgcttcga gaccgcgtgc cacccggacc tggtgctggg      1620
ccgcgcctgc gtccccgagg ccccggagat gggcatcggc gactacctgc cgcccgaggt      1680
gccgcggctc cggcgcgagc cgcccatcgt caccccggag cggtggtcgc cgcacctgag      1740
cgtcctgcgg gccacgccca acgacacggg cctctacacg ctgcacgacg cctcggggcc      1800
gcgggccgtg ttctttgtgg cggtgggcga ccggccgccc gcgccggcgg acccggtggg      1860
ccccgcgcgc cacgagcccc gcttccacgc gctcggcttc cactcgcagc tcttctcgcc      1920
cggggacacg ttcgacctga tgccgcgcgt ggtctcggac atgggcgact cgcgcgagaa      1980
ctttaccgcc acgctggact ggtactacgc gcgcgcgccc ccgcggtgcc tgctgtacta      2040
cgtgtacgag ccctgcatct accaccccgcg cgcgcccgag tgcctgcgcc cggtggaccc      2100
ggcgtgcagc ttcacctcgc cggcgcgcgc gcggctggtg gcgcgccgcg cgtacgcctc      2160
gtgcagcccg ctgctcgggg accggtggct gaccgcctgc cccttcgacg ccttcggcga      2220
ggaggtgcac acgaacgcca ccgcggacga gtcggggctg tacgtgctcg tgatgaccca      2280
caacggccac gtcgccacct gggactacac gctcgtcgcc accgcggccg agtacgtcac      2340
ggtcatcaag gagctgacgg cccggcccg ggccccgggc accccgtggg gccccggcgg       2400
cggcgacgac gcgatctacg tggacggcgt cacgacgccg gcgccgcccg cgcgcccgtg      2460
gaacccgtac ggccggacga cgcccgggcg gctgtttgtg ctggcgctgg gctccttcgt      2520
gatgacgtgc gtcgtcgggg gggccatctg gctctgcgtg ctgtgctccc ggcgccgggc      2580
ggcctcgcgg ccgttccggg tgccgacgcg ggcgcggacg cacatgctct ctccggtgta      2640
caccagcctg cccacgcacg aggactacta cgacggcgac gacgacgacg acgaggaggc      2700
gggcgtcatc cgccggcggc ccgcctcccc cagcggagac agcggctacg aggggccgta      2760
cgcgagcctg gaccccgagg acgagttcag cagcgacgag gacgacgggc tgtacgtgcg      2820
ccccgaggag gcgccccgct ccggcttcga cgtctggttc cgcgatccgg agaaaccgga      2880
agtgacgaat ggacccaact atggcgtgac cgccaaccgc ctgttgatgt cccgccccgc      2940
ttaaataccg ggagaaccgg tccgcccgca ttccgacatg cccggcgccg cctccgtcga      3000
catggacacg ttcgaccccca gcgccccgt cccgacgagc gtctcgaacc cggccgccga     3060
cgtcctgctg gcccccaagg gacccgctc ccgctgcgc cccaggacg actcggactg        3120
ctactacagc gagagcgaca acgagacgcc cagcgagttc ctgcgccgcg tgggacgccg      3180
```
gcaggcggcg cgtcggagac gccgccgctg cctgatgggc gtcgcgatca gcgccaccgc 3240
gctggtcatc tgctcgctgt ccgcgctact cgggggcatc atcgcccggc acgtgtagcg 3300
agcgagcgag cgaacgggag cgggggcccg cccccatccg ccgcgcccag gagagggggg 3360
agagagcggg gggttgggcg cgccacgtgg tgtgggcacg gactcggact tgtcacaata 3420
aatgggcccc ggcgtgtccg ggcgcacaca gcagccttcc tctcctccgc gtctctgttc 3480
cgcccgtctc tcgccggact cttcttctcc accgcctcca ccgtcgcagt tgtcgcgagc 3540
gcgttcgcac catgggggtg acggccatca ccgtggtcac gctgatggac ggggccgggc 3600
gcatccccgc cttcgtgggc gaggcgcacc cggacctgtg gaaggtgctc accgagtggt 3660
gctacgcgtc gatggtgcag cagcggcgcg ccgccgacga gaactcgccg cggcagcacg 3720
tggtgctgcg ctcctcggag atctcccccg gctcgctggc cctgctgccg cgcgccgtgc 3780
gccccgtcgt gcggacgcgg tccgacccca cggcgccgtt ctacatcacc accgagacgc 3840
acgagctgac gcggcgcccc ccggcggacg gctcgaagcc cggggagccc ctcaggatca 3900
gccacccccg cggctggaca cggagtggtc gtccgtcctg aacgggatcc agtacctgaa 3960
ctcgggggcc cggggcacgg ccccgtccac ctgtggatcc tgggcgccgc cgacctctgc 4020
gaccaggtgc tcctggccgc ctcccgcagc accgccgccg gagcctccca cgcccagacg 4080
ggcgcgcgcc tgacccggcg ccggcccggg ctgacggacg ccgacgccct ggacgtgatc 4140
gtcgccggga tccaggcgac ccgcgccatg ttcgcgcggg tccacaaccg ctcctggcgc 4200
cacgccggcg agtggacgga ggccctgcac tcccagatcg tgacccgggg cgacgtgcgc 4260
cggcgccgag gcgggcgcgg caacggacgc gagcgcgccc cgcgatgtac catctcctag 4320

<210> SEQ ID NO 2
<211> LENGTH: 963
<212> TYPE: DNA
<213> ORGANISM: PORCINE PSEUDORABIES VIRUS

<400> SEQUENCE: 2
atgcgcatcc tccggatcta cctcgacggc gcctacggca ccggcaagag caccacggcc 60
cgggtgatgg cgctcggcgg ggcgctgtac gtgcccgagc cgatggcgta ctggcgcact 120
ctgttcgaca cggacacggt ggccggtatt tacgatgcgc agacccggaa gcagaacggc 180
agcctgagcg aggaggacgc ggccctcgtc acggcgcagc accaggccgc cttcgcgacg 240
ccgtacctgc tgctgcacac gcgcctggtc ccgctcttcg ggcccgcggt cgagggcccg 300
cccgagatga cggtcgtctt tgaccgccac ccggtggccg cgacggtgtg cttcccgctg 360
gcgcgcttca tcgtcgggga catcagcgcg gcggccttcg tgggcctggc ggccacgctg 420
cccggggagc cccccggcgg caacctggtg gtggcctcgc tggacccgga cgagcacctg 480
cggcgcctgc gcgcccgcgc gcgcgccggg gagcacgtgg acgcgcgcct gctcacggcc 540
ctgcgcaacg tctacgccat gctggtcaac acgtcgcgct acctgagctc ggggcgccgc 600
tggcgcgacg actgggggcg cgcgccgcgc ttcgaccaga ccgtgcgcga ctgcctcgcg 660
ctcaacgagc tctgccgccc gcgcgacgac cccgagctcc aggacaccct cttcggcgcg 720
tacaaggcgc ccgagctctg cgaccggcgc gggcgcccgc tcgaggtgca cgcgtgggcg 780
atggacgcgc tcgtggccaa gctgctgccg ctgcgcgtct ccaccgtcga cctggggccc 840
tcgccgcgcg tctgcgccgc ggccgtggcg gcgcaggcgc gcggcatgga ggtgacggag 900
tccgcgtacg gcgaccacat ccggcagtgc gtgtgcgcct tcacgtcgga gatgggggtg 960
tga                                                                                                         963

<210> SEQ ID NO 3
<211> LENGTH: 190
<212> TYPE: DNA
<213> ORGANISM: PORCINE PSEUDORABIES VIRUS

<400> SEQUENCE: 3
atgcgcatcc tccggatcta cctcgacggc gcctacggca ccggcaagag caccacggcc    60
cgggtgatgg cgctcggcgg ggcgctgtac gtgcccgagc cgatggcgta ctggcgcact   120
ctgttcgaca cggacacggt ggccggtatt tacgatgcgc agacccggaa gcagaacggc   180
agcctgagcg                                                          190

<210> SEQ ID NO 4
<211> LENGTH: 63
<212> TYPE: PRT
<213> ORGANISM: PORCINE PSEUDORABIES VIRUS

<400> SEQUENCE: 4

Met Arg Ile Leu Arg Ile Tyr Leu Asp Gly Ala Tyr Gly Thr Gly Lys
1               5                   10                  15

Ser Thr Thr Ala Arg Val Met Ala Leu Gly Gly Ala Leu Tyr Val Pro
                20                  25                  30

Glu Pro Met Ala Tyr Trp Arg Thr Leu Phe Asp Thr Asp Thr Val Ala
35 40 45

Gly Ile Tyr Asp Ala Gln Thr Arg Lys Gln Asn Gly Ser Leu Ser
50 55 60

<210> SEQ ID NO 5
<211> LENGTH: 579
<212> TYPE: PRT
<213> ORGANISM: PORCINE PSEUDORABIES VIRUS

<400> SEQUENCE: 5

Met Arg Pro Phe Leu Leu Arg Ala Ala Gln Leu Leu Ala Leu Leu Ala
1 5 10 15

Leu Ala Leu Ser Thr Glu Ala Pro Ser Leu Ser Ala Glu Thr Thr Pro
20 25 30

Gly Pro Val Thr Glu Val Pro Ser Pro Ser Ala Glu Val Trp Asp Asp
35 40 45

Leu Ser Thr Glu Ala Asp Asp Asp Asp Leu Asn Gly Asp Leu Asp Gly
50 55 60

Asp Asp Arg Arg Ala Gly Phe Gly Ser Ala Leu Ala Ser Leu Arg Glu
65 70 75 80

Ala Pro Pro Ala His Leu Val Asn Val Ser Glu Gly Ala Asn Phe Thr
85 90 95

Leu Asp Ala Arg Gly Asp Gly Ala Val Leu Ala Gly Ile Trp Thr Phe
100 105 110

Leu Pro Val Arg Gly Cys Asp Ala Val Ser Val Thr Thr Val Cys Phe
115 120 125

Glu Thr Ala Cys His Pro Asp Leu Val Leu Gly Arg Ala Cys Val Pro
130 135 140

Glu Ala Pro Glu Met Gly Ile Gly Asp Tyr Leu Pro Pro Glu Val Pro
145 150 155 160

Arg Leu Arg Arg Glu Pro Pro Ile Val Thr Pro Glu Arg Trp Ser Pro
165 170 175

```
His Leu Ser Val Leu Arg Ala Thr Pro Asn Asp Thr Gly Leu Tyr Thr
                180                 185                 190

Leu His Asp Ala Ser Gly Pro Arg Ala Val Phe Phe Val Ala Val Gly
            195                 200                 205

Asp Arg Pro Pro Ala Pro Ala Asp Pro Val Gly Pro Ala Arg His Glu
        210                 215                 220

Pro Arg Phe His Ala Leu Gly Phe His Ser Gln Leu Phe Ser Pro Gly
225                 230                 235                 240

Asp Thr Phe Asp Leu Met Pro Arg Val Val Ser Asp Met Gly Asp Ser
                245                 250                 255

Arg Glu Asn Phe Thr Ala Thr Leu Asp Trp Tyr Tyr Ala Arg Ala Pro
            260                 265                 270

Pro Arg Cys Leu Leu Tyr Tyr Val Tyr Glu Pro Cys Ile Tyr His Pro
        275                 280                 285

Arg Ala Pro Glu Cys Leu Arg Pro Val Asp Pro Ala Cys Ser Phe Thr
    290                 295                 300

Ser Pro Ala Arg Ala Arg Leu Val Ala Arg Arg Ala Tyr Ala Ser Cys
305                 310                 315                 320

Ser Pro Leu Leu Gly Asp Arg Trp Leu Thr Ala Cys Pro Phe Asp Ala
                325                 330                 335

Phe Gly Glu Glu Val His Thr Asn Ala Thr Ala Asp Glu Ser Gly Leu
            340                 345                 350

Tyr Val Leu Val Met Thr His Asn Gly His Val Ala Thr Trp Asp Tyr
        355                 360                 365

Thr Leu Val Ala Thr Ala Ala Glu Tyr Val Thr Val Ile Lys Glu Leu
    370                 375                 380

Thr Ala Pro Ala Arg Ala Pro Gly Thr Pro Trp Gly Pro Gly Gly Gly
385                 390                 395                 400

Asp Asp Ala Ile Tyr Val Asp Gly Val Thr Thr Pro Ala Pro Pro Ala
                405                 410                 415

Arg Pro Trp Asn Pro Tyr Gly Arg Thr Thr Pro Gly Arg Leu Phe Val
            420                 425                 430

Leu Ala Leu Gly Ser Phe Val Met Thr Cys Val Val Gly Gly Ala Ile
        435                 440                 445

Trp Leu Cys Val Leu Cys Ser Arg Arg Ala Ala Ser Arg Pro Phe
    450                 455                 460

Arg Val Pro Thr Arg Ala Arg Thr His Met Leu Ser Pro Val Tyr Thr
465                 470                 475                 480

Ser Leu Pro Thr His Glu Asp Tyr Tyr Asp Gly Asp Asp Asp Asp Asp
                485                 490                 495

Glu Glu Ala Gly Val Ile Arg Arg Pro Ala Ser Pro Ser Gly Asp
            500                 505                 510

Ser Gly Tyr Glu Gly Pro Tyr Ala Ser Leu Asp Pro Glu Asp Glu Phe
        515                 520                 525

Ser Ser Asp Glu Asp Gly Leu Tyr Val Arg Pro Glu Glu Ala Pro
    530                 535                 540

Arg Ser Gly Phe Asp Val Trp Phe Arg Asp Pro Glu Lys Pro Glu Val
545                 550                 555                 560

Thr Asn Gly Pro Asn Tyr Gly Val Thr Ala Asn Arg Leu Leu Asn Ala
                565                 570                 575

Arg Pro Ala

<210> SEQ ID NO 6
```

<211> LENGTH: 31
<212> TYPE: DNA
<213> ORGANISM: Unknown
<220> FEATURE:
<223> OTHER INFORMATION: Primer

<400> SEQUENCE: 6
ccggaattct cgtcgtgggc atcgtcatca t                              31

<210> SEQ ID NO 7
<211> LENGTH: 65
<212> TYPE: DNA
<213> ORGANISM: Unknown
<220> FEATURE:
<223> OTHER INFORMATION: Primer

<400> SEQUENCE: 7
ctatctagaa taacttcgta taatgtatgc tatacgaagt tatcggtact gcggaggcta    60
cggac                                                             65

<210> SEQ ID NO 8
<211> LENGTH: 67
<212> TYPE: DNA
<213> ORGANISM: Unknown
<220> FEATURE:
<223> OTHER INFORMATION: Primer

<400> SEQUENCE: 8
acatgcatgc ataacttcgt atagcataca ttatacgaag ttatacggca ggatctctcc    60
gcgtccc                                                           67

<210> SEQ ID NO 9
<211> LENGTH: 32
<212> TYPE: DNA
<213> ORGANISM: Unknown
<220> FEATURE:
<223> OTHER INFORMATION: Primer

<400> SEQUENCE: 9
cccaagctta ggaggggggcg gggagcgcga gc                             32

<210> SEQ ID NO 10
<211> LENGTH: 35
<212> TYPE: DNA
<213> ORGANISM: Unknown
<220> FEATURE:
<223> OTHER INFORMATION: Primer

<400> SEQUENCE: 10
acgcgtcgac tagttattaa tagtaatcaa ttacg                           35

<210> SEQ ID NO 11
<211> LENGTH: 33
<212> TYPE: DNA
<213> ORGANISM: Unknown
<220> FEATURE:
<223> OTHER INFORMATION: Primer

<400> SEQUENCE: 11
acatgcatgc ctagaatgca gtgaaaaaaa tgc                             33

<210> SEQ ID NO 12
<211> LENGTH: 24
<212> TYPE: DNA
<213> ORGANISM: Unknown

<220> FEATURE:
<223> OTHER INFORMATION: Primer

<400> SEQUENCE: 12
tacatcgtcg tgctcgtctt tggc                                       24

<210> SEQ ID NO 13
<211> LENGTH: 21
<212> TYPE: DNA
<213> ORGANISM: Unknown
<220> FEATURE:
<223> OTHER INFORMATION: Primer

<400> SEQUENCE: 13
agctcgtgcg tctcggtggt g                                          21

<210> SEQ ID NO 14
<211> LENGTH: 32
<212> TYPE: DNA
<213> ORGANISM: Unknown
<220> FEATURE:
<223> OTHER INFORMATION: Primer

<400> SEQUENCE: 14
ccggaattcg tagtgccggt tgcccacgta ca                              32

<210> SEQ ID NO 15
<211> LENGTH: 64
<212> TYPE: DNA
<213> ORGANISM: Unknown
<220> FEATURE:
<223> OTHER INFORMATION: Primer

<400> SEQUENCE: 15
ctagtctaga ataacttcgt atagtacaca ttatacgaag ttatcgctca ggctgccgtt   60
ctgc                                                              64

<210> SEQ ID NO 16
<211> LENGTH: 64
<212> TYPE: DNA
<213> ORGANISM: Unknown
<220> FEATURE:
<223> OTHER INFORMATION: Primer

<400> SEQUENCE: 16
acatgcatgc ataacttcgt ataatgtgta ctatacgaag ttataacgac gacggcgtgg   60
gagg                                                              64

<210> SEQ ID NO 17
<211> LENGTH: 30
<212> TYPE: DNA
<213> ORGANISM: Unknown
<220> FEATURE:
<223> OTHER INFORMATION: Primer

<400> SEQUENCE: 17
cccaagctta gggcgacggc gaagaagagc                                  30

<210> SEQ ID NO 18
<211> LENGTH: 35
<212> TYPE: DNA
<213> ORGANISM: Unknown
<220> FEATURE:
<223> OTHER INFORMATION: Primer

```
-continued

<400> SEQUENCE: 18
acgcgtcgac tagttattaa tagtaatcaa ttacg                              35

<210> SEQ ID NO 19
<211> LENGTH: 33
<212> TYPE: DNA
<213> ORGANISM: Unknown
<220> FEATURE:
<223> OTHER INFORMATION: Primer

<400> SEQUENCE: 19
acatgcatgc ctagaatgca gtgaaaaaaa tgc                                33

<210> SEQ ID NO 20
<211> LENGTH: 21
<212> TYPE: DNA
<213> ORGANISM: Unknown
<220> FEATURE:
<223> OTHER INFORMATION: Primer

<400> SEQUENCE: 20
cctacggcac cggcaagagc a                                             21

<210> SEQ ID NO 21
<211> LENGTH: 22
<212> TYPE: DNA
<213> ORGANISM: Unknown
<220> FEATURE:
<223> OTHER INFORMATION: Primer

<400> SEQUENCE: 21
cgcccagcgt cacgttgaag ac                                            22
```

GENE-DELETED VARIANT STRAIN OF PORCINE PSEUDORABIES VIRUS, VACCINE COMPOSITION, METHOD OF MAKING THE SAME AND USE THEREOF

This application is a continuation of U.S. patent application Ser. No. 15/054,404, filed Feb. 26, 2016, which is a continuation of U.S. patent application Ser. No. 14/901,981, filed Dec. 29, 2015, which is a National Stage of PCT/CN2015/070221, filed Jan. 6, 2015, which claims the benefit of priority to CN 201410418379.8, filed Aug. 22, 2014.

FIELD OF THE INVENTION

This invention relates to a gene-deleted variant strain of porcine pseudorabies virus, a vaccine composition prepared therefrom, a method of making the same and a use thereof, belonging to the field of animal virology.

BACKGROUND

Pseudorabies, also called Aujeszky's disease, is an acute infectious disease caused by Suid herpesvirus 1 (SuHV1) belonging to the Alphaherpesvirinae subfamily for many kinds of livestock such as swine, cattle and sheep, as well as poultry and wild animals, with the main symptoms of fever, intense itching (except swine) and encephalomyelitis. Pseudorabies in swine is found nationwide in China causing severe damages, and is one of the major diseases limiting the large-scale production of pig farms. Infection can result in abortion, stillborn or mummified fetuses in pregnant sows, and neurological signs, paralysis and a high death rate in piglets. Pseudorabies virus (PRV) with strong pantropic properties, neurotropic properties and latent infectivity, may establish long-term latent infection in the peripheral nervous system, and then the latently infected host starts to get sick when the latent virus is activated into the infectious virus.

According to recent researches, there are reports of new features of pseudorabies, of which the significant manifestations include that infection among swine at any ages, horizontal transmission among swine herds, short incubation period (1~2 days), morbidity rates between 10%~100%, mortality rate in pigs between 10%~100% (mortality rate in piglets can reach up to 100%), high fever in pigs after being infected (40° C.~42° C., lasting for more than 3 days), dyspnea, diarrhea, wheezing, coughing, sneezing, hind limb paralysis, dog sitting, suddenly falling down, convulsions, lying on their sides, opisthotonus, making strokes with their arms, and finally dying of exhaustion, and the infection also can cause reproductive disorder symptoms such as declined semen quality of boar, as well as abortion of pregnant sow (the abortion rate can reach up to 35%), premature birth, stillbirth, weakened piglets (weakened piglets die by 14 days of age), etc. By means of prior art, vaccinated pigs cannot completely resist attacks by the wild virus, and still have symptoms like high fever, depression, partially or completely loss of appetite, with a infection rate of more than 30% and a mortality rate between 10% and 20%. According to literatures in the prior art, for example, Jin-mei Peng, et al., Identification and antigenic variation of new epidemiology of pseudorabies virus from swine. Chinese Journal of Preventive Veterinary Medicine, 2013, 35(1):1-4; Tong Wu et al., Identification and Characterization of a pseudorabies virus isolated from a dead piglet born to vaccinated sow. Chinese Journal of Animal infectious diseases, 2013, 21(3): 1-7; Yu et al., Pathogenic Pseudorabies Virus, China, 2012. Emerging infectious Diseases. 2014, 20(1):102-104; An et al., Pseudorabies virus variant in Bartha-K61-vaccinated pigs, China, 2012. Emerging infectious Diseases. 2013. 19(11): 1749-1755, there is no vaccines capable of solving the pseudorabies caused by variant strains of porcine pseudorabies virus in the prior art.

The Chinese patent application CN103756977A has disclosed a gE and gI deleted variant strain of porcine pseudorabies virus, PRV-ZJ011G strain (of which the accession number is CGMCC No. 7957) and a vaccine prepared therefrom, of which the content of virus prior to being inactivated is $10^{6.0}TCID_{50}$. Immunization with said vaccine could provide a 100% protection rate for 5 healthy piglets at 45 days of age. Said patent application, however, cannot successfully provide an attenuated live vaccine against new PRV strains, due to both humoral and cellular immunity resulted from proliferation of attenuated live PRV vaccine in vivo.

The Chinese patent application CN103981153A has disclosed the construction of a gene deleted variant strain of the pseudorabies virus labeled with two fluorescent markers, wherein a variant strain of pseudorabies virus with deletion of gE, gI, US9 and TK gene is inserted with GRP gene and RFP gene as labels at the site of deleted genes through homologous recombination. Whereas in this patent application said a gene deleted variant strain is used as a vector of antigen, we don't know if it has immunological competence itself, or how strong the virulence of the variant strain is, since there are more than 70 gene fragments for pseudorabies virus.

It has been disclosed by Chun-Hua Wang et al. (Chun-Hua Wang, Jin Yuan, Hua-Yang Qin, et al, A novel gE-deleted pseudorabies virus (PRV) provides rapid and complete protection from lethal challenge with the PRV variant emerging in Bartha-K61-vaccinated swine population in China, Vaccine 32 (2014)3379-3385) that 6-week-old piglets injected with PRVTJ-$gE^{-}$ live vaccines got a complete protection from challenge and didn't exhibit fever. Whereas as is known to those skilled in the art, the virulence of the PRV live vaccines depends on the age of piglets. Also according to the general experience in the art, the vaccines may not be safe for 7-day-old piglets even though they are safe for 6-week-old piglets. The live vaccines may spread among pigs, therefore the vaccine which is only safe for 6-week-old piglets cannot be ensured to be used clinically and a live vaccine which is safe for 7-day-old piglets, is required in the prior art to prevent effectively infection with the new variant strains of PRV.

SUMMARY OF INVENTION

In order to solve the deficiency of the prior art, the present invention provides an attenuated live strain of porcine pseudorabies virus for prevention and treatment of pseudorabies caused by mutated pseudorabies virus.

The main aim of present invention is to provide an attenuated strain of porcine pseudorabies virus, wherein said attenuated strain of porcine pseudorabies virus is a pseudorabies virus strain with inactivation of gI/gE/11K/28K proteins, preferably said PRV strain is a variant strain of PRV.

The inactivation of gI/gE/11K/28K proteins can be achieved by using well known methods in the art, including deletion of nucleotide sequence expressing the functional fragments of those above proteins from the gene, deletion of the whole ORF from the gene, or deletion or addition of one or more nucleotides whereby the gene cannot express functional proteins normally or the proteins expressed don't have their original function or have an extremely weak function.

As an embodiment of the present invention, the present invention provides an attenuated genetically engineered strain of porcine pseudorabies virus with deletion of gI/gE/11K/28K genes.

As an embodiment of the present invention, the whole ORF of gI/gE/11K/28K genes was deleted from the genome of said attenuated genetically engineered strain of pseudorabies virus.

As an embodiment of the present invention, said variant strain of pseudorabies virus is a virus strain of which gE protein has the sequence of SEQ ID NO:5 or shares at least 95% homology to the sequence of SEQ ID NO:5; preferably, said variant strain of pseudorabies virus is obtained through isolation, and when infection with said variant strain recurs in pigs previously immunized with attenuated gene-deleted strain of pseudorabies virus according to the prior art, the pigs still display clinical signs of infection with said variant strain, selected from high fever, depression and partial or complete loss of appetite; more preferably, said variant strain of pseudorabies virus is a variant strain of pseudorabies virus and when infection with said variant strain recurs in pigs previously immunized with attenuated strain of PRV with deletion of one or more of gE, TK and gI genes, according to the prior art, the pigs are still infected with pseudorabies, which optionally causes clinical signs of infection, selected from depression and loss of appetite among piglets at the age of 9-10 days.

Most preferably, said variant strain of pseudorabies virus, includes, but are not limited to, PRV HN1201 strain (pseudorabies virus, strain HN1201)(deposited in the China Center for Type Culture Collection on May 20, 2013, of which the accession number is CCTCC NO. V 201311 and the address is Wuhan University, Wuhan, China); JS-2012 strain (Wu Tong, Qingzhan Zhang, Hao Zheng et al. Isolation and identification of PRV from piglets infected after immunization [J]. Chinese Journal of Animal Infectious Diseases. 2013, 21(3): 1-7); PRV HeN1 strain (deposited in the China General Microbiological Culture Collection Center on May 20, 2013, of which the accession number is CGMCC NO. 6656 and has been disclosed in the patent application CN102994458A); NVDC-PRV-BJ strain, NVDC-PRV-HEB strain and NVDC-PRV-SD strain (Xiuling Yu, Zhi Zhou, Dongmei Hu, et al. Pathogenic Pseudorabies Virus, China, 2012 Emerging Infectious Diseases, 20, No. 1, January 2014); PRV HN1202 strain (pseudorabies virus, strain HN1202) (deposited in the China Center for Type Culture Collection on Aug. 26, 2013, of which the accession number is CCTCC NO. V 201335 and the address is Wuhan University, Wuhan, China); PRV TJ strain (Chun-Hua Wang Jin Yuan, Hua-Yang Qin, et al, A novel gE-deleted pseudorabies virus (PRV) provides rapid and complete protection from lethal challenge with the PRV variant emerging in Bartha-K61-vaccinated swine population in China. Vaccine. 32 (2014) 3379-3385); a variant strain of pseudorabies virus PRV-ZJ01 (with the accession number, CGMCC No. 8170, and disclosed in CN103627678A).

As an embodiment of the present invention, said PRV strain is HN1201 strain, HN1202 strain, JS-2012 strain, PRV HeN1 strain, NVDC-PRV-BJ strain, NVDC-PRV-HEB strain or NVDC-PRV-SD strain, PRV TJ strain or PRV-ZJ01 strain.

As an embodiment of the present invention, said attenuated strain of porcine pseudorabies virus is an attenuated strain of porcine pseudorabies virus with further inactivation of TK protein; preferably the nucleotide sequence at the location of TK in the genome of said attenuated strain of porcine pseudorabies virus encodes and expresses the amino acid sequence shown in SEQ ID NO:4 of the sequence listing.

As a preferred embodiment of the present invention, the nucleotide sequence at the location of TK in the genome of said attenuated strain of porcine pseudorabies virus is the nucleotide sequence shown in SEQ ID NO:3 of the sequence listing.

As a preferred embodiment of the present invention, the present invention provides an attenuated genetically engineered strain of porcine pseudorabies virus with deletion of gI/gE/11K/28K/TK genes.

As used herein, the term "variant strain of pseudorabies virus", also called highly pathogenic PRV strain, refers to diseases with significant manifestations including infection among swine at any ages, horizontal transmission among swine herds, short incubation period (1~2 days), morbidity rates between 10%~100%, mortality rate in pigs between 10%~100% (mortality rate in piglets can reach up to 100%), high fever of pigs after being infected (40° C.~42° C., lasting for more than 3 days), dyspnea, diarrhea, wheezing, coughing, sneezing, hind limb paralysis, dog sitting, suddenly falling down, convulsions, lying on their sides, opisthotonus, making strokes with their arms, and finally dying of exhaustion, and reproductive disorder symptoms caused by infection such as declined semen quality of boar, as well as abortion of pregnant sow (the abortion rate can reach up to 35%), premature birth, stillbirth, weakened piglets (weakened piglets die by 14 days of age), etc. Preferably, said variant strain of pseudorabies virus obtained through isolation, and when infection with said variant strain recurs in pigs previously immunized with attenuated gene-deleted strain of pseudorabies virus according to the prior art, the pigs still display clinical signs of infection with said variant strain, selected from selected from high fever, depression and partial or complete loss of appetite. Preferably, said variant strain of pseudorabies virus is a virus strain of which gE protein has the sequence of SEQ ID NO:5 or shares at least 95% homology to the sequence of SEQ ID NO:5. More preferably, said variant strain of pseudorabies virus is a variant strain of pseudorabies virus wherein, when infection with said variant strain recurs in pigs previously immunized with attenuated strain of porcine pseudorabies virus with deletion of one or more of gE, TK and gI genes, according to the prior art, the pigs are still infected with pseudorabies, which optionally causes clinical signs of infection selected from depression and loss of appetite among piglets at the age of 9-10 days. The term "homology" in the present invention refers to the level of similarity between two amino acid sequences or two nucleotide sequences. The homology between amino acid sequences or nucleotide sequences can be calculated by any appropriate methods well known in the art, for example, the target amino acid (or nucleotide) sequence and the reference amino acid (or nucleotide) sequence is aligned, and gaps can be induced if necessary to optimize the number of the identical amino acids (or nucleotides) between two aligned sequences, and the percentage of the identical amino acids (or nucleotides) between two aligned sequences can be calculated accordingly. Alignment of amino acid (or nucleotide) sequences and calculation of homology can be achieved by software well kwon in the art. Examples of such software include, but is not limited to, BLAST (which can be accessed through the website of the National Center for Biotechnology Information, NCBI, or can be found in Altschul S. F. et al, J. Mol. Biol, 215:403-410 (1990); Stephen F. et al, Nucleic Acids Res., 25:3389-

3402(1997)), ClustalW2 (which can be accessed through the website of the European Bioinformatics Institute, EBI, or can be found in Higgins D. G. et al, Methods in Enzymology, 266:383-402(1996); Larkin M. A. et al, Bioinformatics (Oxford, England), 23(21):2947-8(2007)), and TCoffee (which can be accessed through the website of the Swiss Institute of Bioinformatics, SIB, or can be found in, Poirot O. et al, Nucleic Acids Res., 31(13):3503-6(2003); Notredame C. et al, J. Mol. Biol, 302(1):205-17(2000)) etc. It is all within the knowledge scope of a person skilled in the art that when using the software to do sequence alignment, he can use the default parameters provided by the software or adjust the parameters provided by the software according to the actual condition.

The term "gI protein" is encoded by US7, and comprises 366 amino acids, with ORF located between 122298-123398.

The term "gE protein" is encoded by US8, and comprises 577 amino acids, with ORF located between 123502-125235.

The term "11K" is encoded by US9, and comprises 98 amino acids, with ORF located between 125293-125589.

The term "28K" is encoded by US2, and comprises 256 amino acids, with ORF located between 125811-126581.

The term "TK", also called thymidine kinase, is encoded by UL23, and comprises 320 amino acids, with ORF located between 59512-60474.

The term "gI/gE/11K/28K" and "gI/gE/11K/28K/TK" in the present invention refers to "gI, gE, 11K and 28K" and "gI, gE, 11K, 28K and TK", respectively, wherein "I" in the present invention refers to "and", for example, "inactivation of gI/gE/11K/28K proteins" refers to inactivation of gI, gE, 11K and 28K proteins.

Unless otherwise stated, the term "PRV-gI-gE-11K-28K-TK-" in the present invention refers to deletion of gI, gE, 11K, 28K and TK genes.

As a preferred embodiment of the present invention, said attenuated genetic strain of porcine pseudorabies virus with deletion of gI/gE/11K/28K genes is attenuated genetically engineered virus strain of PRV HN1201 strain with deletion of gI/gE/11K/28K genes.

As a preferred embodiment of the present invention, said attenuated strain of porcine pseudorabies virus includes HN1201 strain, HN1202 strain, JS-2012 strain, PRV HeN1 strain, NVDC-PRV-BJ strain, NVDC-PRV-HEB strain or NVDC-PRV-SD strain, with deletion of gI/gE/11K/28K.

As a preferred embodiment of the present invention, said attenuated strain of porcine pseudorabies virus is PRV HN1201 strain (pseudorabies virus, strain HN1201) with deletion of gI/gE/11K/28K genes using genetic engineering, wherein said PRV HN1201 strain is deposited in the China Center for Type Culture Collection on May 20, 2013, of which the accession number is CCTCC NO. V 201311 and the address is Wuhan University, Wuhan, China.

As used herein, the term "attenuated" in the present invention refers to: compared with unmodified parent strain, the virulence of the gene-deleted pseudorabies virus strain is reduced, of which manifestations include reduction of numbers of dead pigs, numbers of pigs with fever, and duration of fever. If the statistically significant difference of one or more parameters for determination of severity of diseases for virus strains decreases, its virulence is attenuated.

Another aspect of the invention relates to a vaccine composition, wherein said vaccine composition comprises an immune amount of antigen of said attenuated strain of porcine pseudorabies virus and carrier; preferably the content of antigen of the attenuated strain of porcine pseudorabies virus is not less than $10^{6.0} TCID_{50}/ml$.

As a preferred embodiment of the present invention, the antigen of said attenuated strain of porcine pseudorabies virus is live attenuated strain of porcine pseudorabies virus; said vaccine composition further comprises a cryoprotectant.

As an embodiment of the present invention, said vaccine composition comprises an immune amount of attenuated live vaccine of said variant strain of pseudorabies virus with deletion of gI/gE/11K/28K genes and carrier.

As a preferred embodiment of the present invention, said vaccine composition comprises an immune amount of attenuated live vaccine of said variant strain of pseudorabies virus with deletion of gI/gE/11K/28K/TK genes and carrier.

As a preferred embodiment of the present invention, said vaccine composition comprises an immune amount of attenuated live vaccine of a variant strain of pseudorabies virus with deletion of gI/gE/11K/28K genes, such as HN1201 strain, HN1202 strain, JS-2012 strain, PRV HeN1 strain, NVDC-PRV-BJ strain, NVDC-PRV-HEB strain or NVDC-PRV-SD strain, PRV TJ strain or PRV-ZJ01 strain and carrier.

As a preferred embodiment of the present invention, said vaccine composition comprises an immune amount of attenuated live vaccine of variant strain of PRV strains with deletion of gI/gE/11K/28K/TK genes, such as HN1201 strain, HN1202 strain, JS-2012 strain, PRV HeN1 strain, NVDC-PRV-BJ strain, NVDC-PRV-HEB strain or NVDC-PRV-SD strain, PRV TJ strain or PRV-ZJ01 strain and carrier.

Preferably, the antigen of said attenuated strain of porcine pseudorabies virus is attenuated live PRV strain; said vaccine composition further comprises a cryoprotectant.

As an embodiment of the present invention, said vaccine composition is attenuated live vaccine of the PRV strain with deletion of gI/gE/11K/28K genes.

Optionally, one or more compounds with adjuvant activity may be added to vaccines. It does not necessarily require such an adjuvant to achieve the efficacy of the live attenuated pseudorabies virus according to the present invention, but especially for a combination vaccine comprising the live attenuated pseudorabies virus according to the present invention and antigenic materials from another pathogenic virus or microorganism (see below), it will be worth adding an adjuvant. Adjuvants are non-specific stimulators of the immune system. They improve immune response of the host responding to a vaccine. Examples of adjuvants known in the art is include complete/incomplete Freund's adjuvant, vitamin E, non-ionic blocking copolymers, muramyl dipeptide, ISCOMs (immune stimulating complexes, refer to, for example the European patent EP 1099 42), saponins, mineral oil, vegetable oil, and Carbopol.

Therefore, in a preferred form of said embodiment, the live attenuated vaccine according to the present invention further comprises an adjuvant.

Other examples of pharmaceutically acceptable carriers or diluents can be used in the present invention, include stabilizers such as SPGA, carbohydrates (e.g., sorbitol, mannitol, starch, sucrose, glucose, dextran), proteins such as albumin or casein, protein-containing agents such as bovine serum or skimmed milk and buffers (e.g. phosphate buffer).

Especially when such stabilizers are added to the vaccine, the vaccine is very suitable for freeze-drying. Therefore, in a more preferred form of said embodiment, the live attenuated vaccine is in a freeze-dried form.

In addition, said pseudorabies vaccine in the present invention can be used conjunctly with other inactivated pathogens or antigen to prepare combined vaccines or complex vacancies against various diseases including pseudorabies. As used herein, the term "combined vaccine" refers to a vaccine prepared with the virus mixture by mixing the pseudorabies virus in the present invention with at least one different virus. The term "complex vaccine" refers to a vaccine prepared from viruses and bacterium. For example, the pseudorabies virus in the present invention can be mixed or combined with classical swine fever virus, porcine reproductive and respiratory syndrome virus, porcine circovirus and/or haemophilus parasuis and mycoplasma.

As an embodiment of the present invention, said vaccine further comprises inactivated pathogens or antigen, preferably, said antigen comprises antigen of classical swine fever virus, antigen of porcine reproductive and respiratory syndrome virus, antigen of porcine circovirus and/or haemophilus parasuis or antigen of mycoplasma.

As an embodiment of the present invention, the attenuated virus strain in the present invention can be inserted by exogenous genes, said exogenous genes encode one or more antigens selected from a plurality of pathogens infecting pigs, said pathogens consist of porcine reproductive respiratory syndrome (PRRS) virus, porcine Influenza virus, porcine parvovirus, transmissible gastroenteritis virus, rotavirus, type 1 or type 2 porcine circovirus virus, *Escherichia coli, Erysipelothrix rhusiopathiae, Bordetella bronchiseptica, Haemophilus parasuis, Mycoplasma hyopneumoniae* and *Streptococcus suis*.

Preferably, said vaccine composition may further comprise medium, adjuvants and excipients.

The vaccine composition according to the present invention may also comprises medium, adjuvants and/or excipients. Physiological saline or distilled water can be used as medium.

Another aspect of the present invention relates to a method for preparing said vaccine composition, wherein said method comprises the steps: (1) said attenuated strain of porcine pseudorabies virus is amplified and cultured; and (2) a cryoprotectant is added into said attenuated strain of porcine pseudorabies virus amplified and cultured.

Another aspect of the present invention relates to a use of said vaccine composition for preparing medicine for treatment and prevention of pseudorabies.

As an embodiment of the present invention, said pseudorabies is pseudorabies caused by a variant strain of pseudorabies virus.

As used herein, the term "diseases relating to PRV" can further refer to diseases with significant manifestations including but not limited to infection among swine at any ages, horizontal transmission among swine herds, short incubation period (1~2 days), morbidity rates between 10%~100%, mortality rate in pigs between 10%~100% (mortality rate in piglets can reach up to 100%), high fever of pigs after being infected (40° C.~42° C., lasting for more than 3 days), dyspnea, diarrhea, wheezing, coughing, sneezing, hind limb paralysis, dog sitting, suddenly falling down, convulsions, lying on their sides, opisthotonus, making strokes with their arms, and finally dying of exhaustion, and reproductive disorder symptoms caused by infection such as declined semen quality of boar, as well as abortion of pregnant sow (the abortion rate can reach up to 35%), premature birth, stillbirth, weakened piglets (weakened piglets die by 14 days of age), etc. The differences between above described symptoms and symptoms caused by infection of regular pseudorabies virus in the prior art are: in adult pigs (whose weight is above 50 kg), high fever of infected pigs (40° C.~42° C., lasting for more than 3 days), dyspnea, diarrhea, wheezing, coughing, sneezing, hind limb paralysis, dog sitting, suddenly falling down, convulsions, lying on their sides, opisthotonus, making strokes with their arms, and finally dying of exhaustion; sudden incidence of pseudorabies in newborn piglets and piglets below the age of 4 weeks, further resulting in massive death with a mortality of more than 90%; main manifestations in infected piglets including increased body temperature over 41° C., completely loss of appetite, obvious neurological signs and diarrhea; and in piglets just before or after being weaned, mainly respiratory symptoms, such as dyspnea, coughing and runny noses, etc.

As used herein, the term "prevention" refers to all behaviors to inhibit the infection of pseudorabies virus or delay the onset of the disease via administration of the vaccine composition according to the present invention. The term "treatment" refers to all behaviors to relieve or cure the symptoms caused by infection of PRV via administration of the vaccine composition according to the present invention.

Advantages of the Present Invention

The strain in the present invention with less virulence could provide better immune protection, induce an earlier generation of antibodies and the challenge result after immunization shows that gE antibody is still negative.

BRIEF DESCRIPTION OF THE DRAWINGS

FIG. 1 is a schematic diagram showing construction of plasmid pUCgI/gE/11K/28KA-GFP-B;

FIG. 2 is a schematic diagram showing the location for deletion of gI/gE/11K/28K genes and location of homologous arms, USA and USB in the genome;

FIG. 3 is a gel electrophoresis pattern for comparing PCR fragments of PRV HN1201 strain before and after deletion of gI/gE/11K/28K genes through PCR method;

FIG. 4 is a schematic diagram showing the location for deletion of TK gene and location of homologous arms of TKA and TKB in the genome;

FIG. 5 is a gel electrophoresis pattern for comparing PCR fragments of PRV HN1201 strain before and after deletion of TK gene through PCR method.

SEQUENCE LISTING

SEQ ID NO:1 is the nucleotide sequence of gI/gE/11K/28K genes in the PRV HN1201 strain.

SEQ ID NO:2 is the nucleotide sequence of TK gene in the PRV HN1201 strain.

SEQ ID NO:3 is the nucleotide sequence of location for deletion of TK gene in the PRV HN1201 strain.

SEQ ID NO:4 is the amino acid sequence of location for deletion of TK gene in the PRV HN1201 strain.

SEQ ID NO:5 is the amino acid sequence of gE in the PRV HN1201 strain.

DETAILED DESCRIPTION

The description of the present invention is further provided as follows with reference to the specific embodiments, and features and advantages of the present invention will become more apparent from the following description. However, these embodiments are only exemplary, but not forming any limitation to the scope of the present invention.

It should be understood by a person skilled in the art that modifications or alternatives to details and forms of the technical solution of the present invention without deviation from the spirit and scope of the present invention will be allowed, while those modification and alternatives should all fall within the scope of the present invention.

In the invention, the term "per pig" refers to the amount of vaccine each pig injected.

In the invention, the term "TCID$_{50}$" refers to 50% tissue culture infective dose, a way to represent viral infectivity.

Minimum Essential Medium (MEM) liquid medium is prepared with MEM dry powdered medium purchased from Life Technologies, Corp. according to the instruction.

Dulbecco's Modified Eagle's Medium (DMEM) in the present invention is prepared with reference to the preparation method from Appendix A of GB/T18641-2002 *Diagnostic Techniques for Aujeszk's Disease*.

In the present invention, the term "PBS" is the abbreviation for Phosphate Buffer Saline, and 0.01 mM pH 7.4 PBS as used in the present invention is prepared as described in *Molecular cloning: Laboratory manuals*, 3rd edition.

The PRV HN1201 strain (pseudorabies virus, strain HN1201) used in the embodiments is deposited in the China Center for Type Culture Collection on May 20, 2013, of which the accession number is CCTCC NO. V 201311 and the address is Wuhan University, Wuhan, China.

The PRV HN1202 strain (pseudorabies virus, strain HN1202) used in the embodiments is deposited in the China Center for Type Culture Collection on Aug. 26, 2013, of which the accession number is CCTCC NO. V 201335 and the address is Wuhan University, Wuhan, China.

PRV is the abbreviation for the term Pseudorabies virus.

In the following specific embodiments, the description of the present invention is further provided with examples of PRV HN1201 strain, NVDC-PRV-BJ strain, NVDCPRV-HEB strain, NVDC-PRV-SD strain and HN1202 strain.

Example 1

Preparation of PRV HN1201 Strain with Deletion of gI/gE/11K/28K 1.1 Construction of a Transfer Vector for Recombinant PRV HN1201GFP Virus According to the sequence of US segment (gI/gE/11K/28K) to be deleted, the homologous arms were designed at its two ends, called USA and USB, respectively. USA and USB were cloned into pUC19 vector and named pUCUSAB. Then GFP gene was cloned into pUCUSAB, to obtain a transfer vector for recombinant virus which was called pUCUSA-GFP-B. The homologous arms in the transfer vector are sequences of two sides of US, therefore the recombinant virus obtained after recombination, was US segment deleted, which comprised gI/gE/11K/28K. FIG. 1 is a schematic diagram showing construction of the transfer vector, and FIG. 2 shows the location of the homologous arms, USA and USB in the genome.

1.1.1 Amplification and Cloning of the Homologous Recombinant Arms 1.1.1.1 Design of Primers and Preparation of Templates Two pairs of primers were designed for amplifying the homologous arms at two sides of segment to be deleted according to the gene sequence of HN1201 virus:

The upstream and downstream primers for the homologous arm USA at the left side are, respectively:

SEQ ID NO: 6
USAF: CCG<u>GAATTC</u>TCGTCGTGGGCATCGTCATCAT
(the underline portion refers to the EcoR I cutting site), SEQ ID NO: 7
USAR: CTA<u>TCTAGA</u>ataacttcgtataatgtatgctatacgaagttat
CGGTACTGCGGAGGCTACGGAC
(the underline portion refers to the Xba I cutting site, lowercase letters refer to the loxp site, The upstream and downstream primers for the homologous arm USB at the right side are, respectively:

SEQ ID NO: 8
USBF: ACAT<u>GCATGC</u>ataacttcgtatagcatacattatacgaagttat
ACGGCAGGATCTCTCCGCGTCCC
(the underline portion refers to the SphI cutting site, lowercase letters refer to the loxp site), SEQ ID NO: 9
USBR: CCC<u>AAGCTT</u>AGGAGGGGCGGGGAGCGCGAGC
(the underline portion refers to the Hind III cutting site), Vero cells were transfected with PRV HN1201, and part of supernatant was harvested when the cytopathic effect of cells reached to 80%, for extracting genomic DNA of virus by using Geneaid Viral Nucleic Acid Extraction kit as the template for amplification of the homologous arms.

1.1.1.2 Amplification and Cloning of the Homologous Arms, USA and USB

USA and USB were amplified through PCR method by using TAKARA PrimeSTAR, of which the system and condition is as follows:

| PRV HN1201 DNA | 1 μL |
| PrimeSTAR | 0.5 μL |
| 2*primeSTAR GC buffer | 25 μL |
| dNTP(25 mM) | 4 μL |
| Upstream primer | 0.5 μL |
| downstream primer | 0.5 μL |
| Water | Used for adjusting to a final volume of 50 μL |

| 98° C. | 2 min | |
| 98° C. | 10 s | |
| 68° C. | 1 min 15 s | } 30 cycles |
| 68° C. | 5 min | |

USA and USB fragments amplified by PCR were separated by electrophoresis on agarose gel, and the target fragments were recovered with TIANGEN Gel Recovery Kit. USA fragment and pUC19 vector was digested by both of EcoR I and XbaI, and the target fragments were recovered, connected by T4 DNA ligase, and the product was transformed into DH5α. The transformation mix was spread onto plates containing ampicillin, and incubated at 37° C. overnight. A single colony was picked to extract the plasmid and the plasmid was identified using enzyme digestion, and the correct plasmid after identification was named pUCUSA. pUCUSA and USB was digested by both of SalI and HindIII, and the target fragments were recovered, linked by T4 DNA ligase, and the product was transformed into DH5α. The transformation mix was spread onto plates containing ampicillin, and incubated at 37° C. overnight. A single colony was picked to extract the plasmid and the plasmid was identified by sequencing after enzyme digestion, and the correct plasmid after identification was named pUCUSAB.

1.1.3 Amplification of Label Gene GFP

1.1.2.1 Removal of Multiple Cloning Site (MCS) of GFP Vector pAcGFP-C1

The pAcGFP-C1 plasmid (purchased from Clontech, Catalog No. 632470) was digested by Bgl II and Sma I, and the linearized vector was recovered, linked by T4 DNA Ligase after filling-in with DNA Polymerase I Large (Klenow) Fragment, and transformed into the competent cell DH5α to obtain MCS deleted GFP plasmid, named pAcGFPΔMCS.

1.1.2.2 Amplification of GFP Gene

The primers for amplifying GFP were designed according to the sequence of pAcGFP-C1 vector.

Upstream Primer

```
                                    SEQ ID NO: 10
CMVU: ACGCGTCGACTAGTTATTAATAGTAATCAATTACG
(the underline portion refers to the SalI
cutting site.),
```

Downstream Primer

```
                                    SEQ ID NO: 11
SV40R: ACATGCATGCCTAGAATGCAGTGAAAAAAATGC
(the underline portion refers to the Sph I
cutting site.),
```

GFP gene was amplified with pAcGFPΔMCS plasmid as the template, of which the system and condition is as follows:

| | |
|---|---|
| pAcGFPΔMCS | 1 μL |
| primeSTAR | 0.5 μL |
| 2*primeSTAR GC buffer | 25 μL |
| dNTP(25 mM) | 4 μL |
| Upstream primer CMVU | 0.5 μL |
| Downstream primer SV40R | 0.5 μL |
| Water | Used for adjusting to a final volume of 50 μL |

| | | |
|---|---|---|
| 94° C. | 2 min | |
| 94° C. | 30 s | |
| 60° C. | 30 s | 30 cycles |
| 72° C. | 2 min | |
| 72° C. | 5 min | |

A target band was recovered by electrophoresis on agarose gel for further linking.

1.1.3 Linking of GFP Label Gene and pUCUSAB

GFP was digested with both of Sal and Sph I, and the target fragments were recovered, linked to pUCUSB plasmid which had been through the same double enzyme digestion, and the product was transformed into the competent cell DH5α. The transformation mix was spread onto plates containing ampicillin, and incubated at 37° C. overnight. A single colony was picked to extract the plasmid and the plasmid was identified by sequencing after enzyme digestion, and the correct plasmid after identification was named pUCUSA-GFP-B.

1.2 Acquisition of Recombinant Virus Containing GFP

1.2.1 Acquisition of Recombinant Virus Through Co-Transfection of Vero Cells with the Transfer Vector and HN1201 DNA Co-transfection of vero cells was conducted by using lipofectin technique, wherein 3 μg PRV-HN1201 viral genomic DNA and 5 μg the transfer vector pUCUSA-GFP-B was transfected, in accordance with procedures of Lipofectamine 2000 Protocol (Invitrogen, Catalog No. 11668030). Cells were incubated at 37° C. in an incubator containing 5% $CO_2$. The supernatant of cell culture, i.e. P0 recombinant virus, named rPRV-GFP-US-, was collected 36-48h after transfection, or until the cytopathic effect was visible and infected cells exhibited fluorescence.

1.2.2 Plaque Purification of Recombinant Viruses

When infected with the obtained P0 recombinant virus rPRV-GFP-US-, vero cells infected were covered with 2% agarose with low melting point. After 48h when the cytopathic effect became apparent and infected cells exhibited obvious fluorescence, a plaque with a green fluorescence was picked and freeze-thawed 3 times in −70° C., inoculated at 10-fold serial dilutions into vero cells previously laid in six-well plates. Such plaque with a green fluorescence was continued to be picked for purification. After 8 rounds of plaques purification, a purified recombinant virus rPRV-GFP-US- which was free of wild-type virus HN1201 and with deletion of gI/gE/US9/US2 (i.e. gI/gE/11K/28K) was obtained.

1.3 Deletion of GFP Label Gene in the gI/gE/US9/US2 (i.e. gI/gE/11K/28K) Segment-Deleted Recombinant Virus pBS185 plasmid expressing Cre enzyme (purchased from addgene, Cre enzyme recognizes loxP sites at downstream of USA and upstream of USB, wherein USA and USB are homology arms, and deletes sequence between two loxp sites) and genomic DNA of recombinant virus rPRV-GFP-US- was co-transfected into vero cells, with the results showing relatively obvious cytopathic effect and more single fluorescence 24h after transfection. After serial dilution, P0 virus harvested was inoculated for plaque screening; fluorescence-negative plaque was picked for the next round of purification. After 2 rounds of screening and purification, a fluorescence-negative virus was obtained, and named vPRV-US-. PCR identification result after extraction and purification of viral genomic DNA, showed deletion of gI/gE/US9/US2 (i.e. gI/gE/11K/28K) segment, and indicated that GFP label gene had been deleted. The result showed a successful purification of gI/gE/US9/US2 (i.e. gI/gE/11K/28K) segment-deleted virus containing no GFP label gene.

1.4 Confirmation of PRV HN1201 Strain with Deletion of US Segment

The viral genome of gI/gE/US9/US2 (i.e. gI/gE/11K/28K) segment-deleted virus and wild-type virus, was extracted and identified by PCR, with the following primers:

```
                                    SEQ ID NO: 12
    USDCF:
    TACATCGTCGTGCTCGTCTTTGGC,

SEQ ID NO: 13
    USDCR:
    AGCTCGTGCGTCTCGGTGGTG,
```

The size of PCR amplification product of the wild-type virus was 6286 bp, the size of PCR amplification fragment of gI/gE/US9/US2 (i.e. gI/gE/11K/28K) segment-deleted virus was 1960 bp.

PCR assay result confirmed that ORF of gI/gE/US9/US2 (i.e. gI/gE/11K/28K) segment had been completely missing.

Example 2

Preparation of PRV HN1201 Strain with Deletion of gI/gE/11K/28K/TK

2.1 Construction of a Transfer Vector for Recombinant PRV HN1201GFP Virus

According to the sequence of TK gene to be deleted, the homologous arms at its two ends were designed, called TKA and TKB, respectively. TKA and TKB were cloned into pUC19 vector and named pUCTKAB. Then GFP gene was cloned into pUCTKAB, to obtain a transfer vector for recombinant virus which was called pUCTKA-GFP-B. The homologous arms in the transfer vector are sequences of two sides of TK, therefore the recombinant virus obtained after recombination, was TK gene deleted. FIG. 4 shows the location of homologous arms, TKA and TKB in the genome.

2.1.1 Amplification and Cloning of the Homologous Recombinant Arms 2.1.1.1 Design of Primers and Preparation of Template Two pairs of primers were designed for amplifying the homologous arms at two sides of TK gene according to the gene sequence of HN1201 virus:

The upstream and downstream primers for the homologous arm TKA at the left side are, respectively:

```
                                              SEQ ID NO: 14
TKAF:
CCGGAATTCGTAGTGCCGGTTGCCCACGTACA
(the underline portion refers to the EcoR I
cutting site), SEQ ID NO: 15
TKAR:
CTAGTCTAGAataacttcgtatagtacacattatacgaagttat
CGCTCAGGCTGCCGTTCTGC
(the underline portion refers to the Xba I
cutting site, lowercase letters refer to
the loxp site),
```

The upstream and downstream primers for the homologous arm TKB at the right side are, respectively:

```
                                              SEQ ID NO: 16
TKBF:
ACATGCATGCataacttcgtataatgtgtactatacgaagttat
AACGACGACGGCGTGGGAGG
(the underline portion refers to the SphI
cutting site, lowercase letters refer to
the loxp site), SEQ ID NO: 17
TKBR:
CCCAAGCTTAGGGCGACGGCGAAGAAGAGC
(the underline portion refers to the Hind III
cutting site),
```

Vero cells were transfected with PRV HN1201, and part of supernatant was harvested when the cytopathic effect of cells reached to 80%, for extracting genomic DNA of virus by using Geneaid Viral Nucleic Acid Extraction kit as the template for amplification of the homologous arms.

2.1.1.2 Amplification and Cloning of the Homologous Arms, TKA and TKB

TKA and TKB were amplified through PCR method by using TAKARA PrimeSTAR, of which the system and condition is as follows:

| | |
|---|---|
| PRV HN1201 DNA | 1 μL |
| PrimeSTAR | 0.5 μL |
| 2*primeSTAR GC buffer | 25 μL |
| dNTP(25 mM) | 4 μL |
| Upstream primer | 0.5 μL |
| downstream primer | 0.5 μL |
| Water | Used for adjusting to a final volume of 50 μL |

| | | |
|---|---|---|
| 98° C. | 2 min | |
| 98° C. | 10 s | 30 cycles |
| 68° C. | 1 min 15 s | 30 cycles |
| 68° C. | 5 min | |

TKA and TKB fragments amplified by PCR were separated by electrophoresis on agarose gel, and the target fragments were recovered with TIANGEN Gel Recovery Kit. TKA fragment and pUC19 vector was digested with both of EcoR I and XbaI, and the target fragments were recovered, linked by T4 DNA ligase, and the product transformed into DH5α. The transformation mix was spread onto plates containing ampicillin, and incubated at 37° C. overnight. A single colony was picked to extract the plasmid and the plasmid was identified after enzyme digestion, and the correct plasmid after identification was named pUCTKA. pUCTKA and TKB was digested with both of SalI and HindIII, and the target fragments were recovered, linked by T4 DNA ligase, and the product transformed into DH5α. The transformation mix was spread onto plates containing ampicillin, and incubated at 37° C. overnight. A single colony was picked to extract the plasmid and the plasmid was identified by sequencing after enzyme digestion, and the correct plasmid after identification was named pUCTKAB.

2.1.2 Amplification of Label Gene GFP 2.1.2.1 Removal of Multiple Cloning Site (MCS) of GFP Vector pAcGFP-C1

The pAcGFP-C1 plasmid (purchased from Clontech, Catalog No. 632470) was digested with Bgl II and Sma I, and the linearized vector was recovered, linked by T4 DNA Ligase after filling-in with DNA Polymerase I Large (Klenow) Fragment, and the product was transformed into the competent cell DH5α to obtain MCS deleted GFP plasmid, named pAcGFPΔMCS.

2.1.2.2 Amplification of GFP Gene

The primers for amplifying GFP were designed according to the sequence of pAcGFP-C1 vector.

Upstream primer

```
                                              SEQ IDD NO: 18
CMVU:
ACGCGTCGACTAGTTATTAATAGTAATCAATTACG
(the underline portion refers to the SalI
cutting site.),
```

Downstream primer

```
                                              SEQ ID NO: 19
SV40R:
ACATGCATGCCTAGAATGCAGTGAAAAAAATGC
(the underline portion refers to the Sph I
cutting site.),
```

GFP gene was amplified with the template of pAcGFPΔMCS plasmid, of which the system and condition is as follows:

| | |
|---|---|
| pAcGFPΔMCS | 1 μL |
| PrimeSTAR | 0.5 μL |
| 2*primeSTAR GC buffer | 25 μL |
| dNTP(25 mM) | 4 μL |
| Upstream primer CMVU | 0.5 μL |
| Downstream primer SV40R | 0.5 μL |
| Water | Used for adjusting to a final volume of 50 μL |

| | | |
|---|---|---|
| 94° C. | 2 min | |
| 94° C. | 30 s | |
| 60° C. | 30 s | 30 cycles |
| 72° C. | 2 min | |
| 72° C. | 5 min | |

A target band was recovered by electrophoresis on agarose gel for further linking.

2.1.3 Linking of GFP Label Gene and pUCTKAB

GFP was digested with both of Sal and Sph I, and the target fragments were recovered, linked to pUCTKAB plasmid which had been through the same double enzyme digestion, and the linked product was transformed into the competent cell DH5α. The transformation mix was spread onto plates containing ampicillin, and incubated at 37° C. overnight. A single colony was picked to extract the plasmid and the plasmid was identified by sequencing after enzyme digestion, and the correct plasmid after identification was named pUCTKA-GFP-B.

2.2 Acquisition of Recombinant Virus Containing GFP 2.2.1 Acquisition of Recombinant Virus Through Co-Transfection of Vero Cells with the Transfer Vector and vPRV-gI-gE-11K-28K-DNA Co-transfection of vero cells was conducted by using lipofectin technique, wherein 3 μg vPRV-gI-gE-11K-28K-viral genomic DNA and 5 μg the transfer vector pUCTKA-GFP-B was transfected, in accordance with procedures of Lipofectamine 2000 Protocol (Invitrogen, Catalog No. 11668030). Cells were incubated at 37° C. in an incubator containing 5% $CO_2$. The supernatant of cell culture, i.e. P0 recombinant virus, named rPRV-GFP-gI-gE-11K-28K-TK-, was collected 36-48h after transfection, or until the cytopathic effect was visible and infected cells exhibited fluorescence.

2.2.2 Plaque Purification of Recombinant Virus rPRV-GFP-gI-gE-11K-28K-TK-

When infected with the obtained P0 recombinant virus rPRV-GFP-gI-gE-11K-28K-TK-, vero cells infected were covered with 2% agarose with low melting point. After 48h when the cytopathic effect became apparent and infected cells exhibited obvious fluorescence, a plaque with a green fluorescence was picked and freeze-thawed 3 times in −70° C., inoculated at 10-fold serial dilutions into vero cells previously laid in six-well plates. Such plaque with a green fluorescence was continued to be picked for purification. After 11 rounds of plaques purification, a purified recombinant virus rPRV-GFP-gI-gE-11K-28K-TK- which was free of PRV-gI-gE-11K-28K-TK- and with deletion of five genes was obtained.

2.3 Deletion of GFP Label Gene in gI/gE/11K/28K/TK Deleted Recombinant Virus

The pBS185 plasmid expressing Cre enzyme (purchased from addgene, Cre enzyme recognizes mutated loxP sites at downstream of TKA and upstream of TKB, wherein TKA and TKB are homology arms, and deletes sequence between two loxp sites) and genomic DNA of recombinant virus rPRV-GFP-gI-gE-11K-28K-TK- was co-transfected into vero cells, with the results showing relatively obvious cytopathic effect and more single fluorescence 24h after transfection. After serial dilution, P0 virus harvested was inoculated for plaque screening; fluorescence-negative plaque was picked for the next round of purification. After 2 rounds of screening and purification, a fluorescence-negative virus was obtained, and named PRV-gI-gE-11K-28K-TK-. PCR identification result after extraction and purification of viral genomic DNA, showed deletion of TK gene, and also indicated that GFP label gene had been deleted. The result showed a successful purification of gI-gE-11K-28K-TK-deleted virus containing no GFP label gene.

2.4 Confirmation of PRV HN1201 Strain with Deletion of gI/gE/11K/28K/TK

The primers used for identifying deletion of gI/gE/11K/28K were the same as above.

The viral genome of gI/gE/11K/28K/TK-deleted virus and wild-type virus, was extracted and identified by PCR, with the following primers:

TKDCF:
cctacggcaccggcaagagca,    SEQ ID NO: 20

TKDCR:
cgcccagcgtcacgttgaagac,    SEQ ID NO: 21

The size of PCR amplification product of the wild-type virus was 1566 bp, the size of PCR amplification fragment of TK deleted virus was 742 bp (refer to FIG. 5).

Example 3

Preparation of PRV HN1201 Strain with Deletion of gI/gE

PRV HN1201 strain with deletion of gI/gE was prepared by reference to the method in Example 1 of CN103756977A.

Example 4

Pathogenicity Test of Gene-Deleted PRV Strain 25 7-day-old piglets which were negative for pseudorabies antibodies and pseudorabies antigen were randomly divided into 5 groups (A, B, C, D and blank control group), each with 5 piglets. Grouping conditions and challenge conditions are shown in Table 1.

TABLE 1

Grouping of animals in the pathogenicity test

| Group | Strain used for inoculation | Dose |
|---|---|---|
| A | PRV HN1201 strain with deletion of gI/gE/11K/28K prepared in Example 1 | inoculated with 1 ml ($10^{7.0}TCID_{50}$/ml)/piglet by intranasal instillation |
| B | PRV HN1201 strain with deletion of gI/gE/11K/28K/TK prepared in Example 2 | inoculated with 1 ml ($10^{7.0}TCID_{50}$/ml)/piglet by intranasal instillation |
| C | PRV HN1201 strain with deletion of gI/gE prepared in Example 3 | inoculated with 1 ml ($10^{7.0}TCID_{50}$/ml)/piglet by intranasal instillation |
| D | PRV HN1201 strain | inoculated with 1 ml ($10^{7.0}TCID_{50}$/ml)/piglet by intranasal instillation |
| Blank control | DMEM medium | inoculated with 1 ml/piglet by intranasal instillation |

After inoculation of virus, the temperature of piglets was determined daily, and clinical signs and death status were observed. The results are shown in Table 2.

TABLE 2

Pathogenicity of different genes-deleted PRV HN1201 strains in 7-day-old piglets

| Group | Number | Clinical signs | Death status |
|---|---|---|---|
| A | A1 | Normal body temperature, no clinical signs | Survived |
|  | A2 | Body temperature increased for 1 day, no clinical signs | Survived |
|  | A3 | Normal body temperature, no clinical signs | Survived |
|  | A4 | Normal body temperature, no clinical signs | Survived |
|  | A5 | Body temperature increased for 1 day, no clinical signs | Survived |
| B | B1 | Normal body temperature, no clinical signs | Survived |
|  | B2 | Normal body temperature, no clinical signs | Survived |
|  | B3 | Normal body temperature, no clinical signs | Survived |
|  | B4 | Normal body temperature, no clinical signs | Survived |
|  | B5 | Normal body temperature, no clinical signs | Survived |
| C | C1 | Body temperature increased for 1 day, slightly depression, loss of appetite | Survived |
|  | C2 | Body temperature increased for 1 day, slightly depression, loss of appetite | Survived |
|  | C3 | Body temperature increased for 1 day, slightly depression, loss of appetite | Survived |
|  | C4 | Body temperature increased for 1 day, slightly depression, loss of appetite | Survived |
|  | C5 | Body temperature increased for 1 day, slightly depression, loss of appetite | Survived |
| D | D1 | Body temperature increased for 3 days, depression, completely loss of appetite, neurological signs such as staying lying, dyspnea, trembling, convulsions, turning around, and making strokes with their arms | Died on day 3 after challenge |
|  | D2 | Body temperature increased for 4 days, depression, completely loss of appetite, staying lying, dyspnea, trembling and convulsions. | Died on day 4 after challenge |
|  | D3 | Body temperature increased for 4 days, depression, completely loss of appetite, neurological signs such as staying lying, dyspnea, trembling, convulsions, turning around, and making strokes with their arms | Died on day 4 after challenge |
|  | D4 | Body temperature increased for 4 days, depression, completely loss of appetite, neurological signs such as staying lying, dyspnea, trembling, convulsions, turning around, and making strokes with their arms | Died on day 4 after challenge |
|  | D5 | Body temperature increased for 4 days, depression, completely loss of appetite, neurological signs such as staying lying, dyspnea, trembling, convulsions, and making strokes with their arms | Died on day 4 after challenge |
| Blank control | K1 | Normal | Survived |
|  | K2 | Normal | Survived |
|  | K3 | Normal | Survived |
|  | K4 | Normal | Survived |
|  | K5 | Normal | Survived |

It showed in the results that inoculation with PRV HN1201 strain in 7-day-old piglets could lead to 100% death (5/5) of inoculated piglets, while the virulence of PRV HN1201 strain with deletion of gI/gE/11K/28K was significantly decreased, which could only make the temperature of 2 piglets increased, without any clinical signs. Inoculation with PRV HN1201 strain with deletion of gI/gE in 7-day-old piglets could still lead to common clinical signs such as increased body temperature and depression etc., indicating remaining virulence; while PRV HN1201 strain with deletion of gI/gE/11K/28K/TK gene had completely lost its virulence.

Example 5

Preparation of the Live Gene-Deleted PRV Vaccines 5.1 Proliferation of Vaccine Virus The virus seed of PRV HN1201 strain with deletion of gI/gE/11K/28K prepared in Example 1, PRV HN1201 strain with deletion of gI/gE/11K/28K/TK prepared in Example 2 and PRV HN1201 strain with deletion of gI/gE prepared in Example 3 was diluted at $5 \times 10^4$ fold, and then inoculated into a monolayer of ST cell. After 1 h adhesion, 1000 ml of DMEM medium containing 2% fetal calf serum was added into ST cell, which was then placed at 37° C. in a roller bottle with a rotation speed of 6 rph. The cell medium containing viruses was harvested when the cytopathic effect of cells reached to 80%; the viruses were harvested after 2 times of freezing-thawing the medium and the virus titer was assessed. The virus solution was preserved at low temperature.

5.2 Preparation of a Protective Agent 40 g of sucrose and 8 g of gelatin was added into every 100 ml of deionized water, and the solution was autoclaved (under 121° C. for 30 min) after fully melted.

5.3 Preparation of Vaccine Virus Suspension

The virus solution prepared and preserved in Example 5.1 was mixed with the protective agent prepared and preserved in Example 5.2 at a volume ratio of 1:1, distributed into sterilized bottles, each of which containing 2.6 ml and the mixed virus solution was freeze-dried. The vaccine was tested and determined to be free of contamination of bacterium and exogenous viruses and the content of virus was consistent with that before freeze-drying. The batch number of PRV HN1201 strain with deletion of gI/gE/11K/28K prepared in Example 1, PRV HN1201 strain with deletion of gI/gE/11K/28K/TK prepared in Example 2 and PRV HN1201 strain with deletion of gI/gE prepared in Example 3 were 20140501, 20140502 and 20140503, respectively.

Example 6

Immunogenicity Assay of the Live Gene-Deleted PRV Vaccines 12 9-day-old piglets which were negative for PRV antibodies and PRV antigens were randomly divided into 5 groups, each with 5 piglets, and the piglets were injected with the vaccines prepared in Example 5 according to Table 3. The vaccine control group was inoculated with the live PRV vaccine, Bartha K-61strain purchased from HIPRA, Spain, Batch No. 42RH, at the dosage from the protocol. The blank control group was inoculated with 1 mL/piglet of DMEM medium. The piglets were challenged with $1 \times 10^{7.0}$ TCID$_{50}$/piglet of PRV HN1201 strain on day 28 after immunization. After challenge, the body temperature of piglets was determined daily, and in the meanwhile clinical signs and death status were observed (The results are shown in Table 3), the blood of piglets in all the experimental groups and control groups was collected respectively before challenge.

TABLE 3

Grouping of animals in the pathogenicity test

| Group | Vaccines injected | Dose |
|---|---|---|
| Group I | Batch No. 20140501 | inoculated with 1 ml $10^{6.0}TCID_{50}$/piglet by intramuscular injection |
| Group II | Batch No. 20140502 | inoculated with 1 ml $10^{6.0}TCID_{50}$/piglet by intramuscular injection |
| Group III | Batch No. 20140503 | inoculated with 1 ml $10^{6.0}TCID_{50}$/piglet by intramuscular injection |
| Vaccine control group 2 | Live PRV vaccine | inoculated with 2 ml $10^{6.0}TCID_{50}$/piglet by intramuscular injection |
| Blank control group | DMEM medium | inoculated with 1 mL/piglet by intramuscular injection |

The piglets were challenged with 1□$10^{7.0}TCID_{50}$/piglet (1 ml/piglet) of PRV HN1201 strain on day 28 after immunization. After challenge, the body temperature of piglets was determined daily, and in the meanwhile clinical signs and death status were observed (The results are shown in Table 5).

TABLE 5 clinical status and challenge status for piglets challenged after immunization with live PRV vaccines

| Group | clinical signs and death status | Rate of protection |
|---|---|---|
| Group I | Normal body temperature, normal appetite, no abnormal clinical signs, survived | 100% (5/5) |
| Group II | Normal body temperature, normal appetite, no abnormal clinical signs, survived | 100% (5/5) |
| Group III | After immunization, body temperature increased, slightly depression and loss of appetite. After challenge, normal body temperature, normal appetite, no abnormal clinical signs, survived | 100% (5/5) |
| Vaccine control group | Body temperature of three piglets increased for 7-10 days, depression, loss of appetite, one died. | 80% (4/5) |
| Blank control group | Body temperature of three piglets increased for 7-10 days, depression in all piglets, partially or completely loss of appetite, significant clinical signs, two piglets died on day 4 after challenge, and all died within 5 days after challenge. | 0% (0/5) |

The result from Table 5 indicated that immunizing piglets with the gene-deleted PRV vaccines prepared in example 5 can blocked virus infection (i.e. displaying clinical signs), and provide 100% (5/5) protection rate for piglets, while all the piglets in the blank control group died by day 5 after challenge, therefore the PRV vaccines in three experimental groups can provide excellent protection, showing excellent immune protection and safety; meanwhile it indicated that either deletion of gI/gE/11K/28K or deletion of gI/gE/11K/ 28K/TK for PRV strain would not affect the immunogenicity. For the vaccine group with only deletion of gI/gE, the clinical signs such as increased body temperature could not be avoided, while the vaccine still possessed good immunogenicity. Whereas the commercial vaccines in the prior art cannot provide a full protection to pigs.

Example 7

Construction of Gene-Deleted Variant Strains of NVDC-PRV-BJ Strain, NVDCPRV-HEB Strain and NVDC-PRV-SD Strain, HN1202 PRV Variant Strain gI/gE/11K/28K genes and gI/gE/11K/28K/TK genes were deleted from the parent strains, NVDC-PRV-BJ strain, NVDC-PRV-HEB strain and NVDC-PRV-SD strain (Xiuling Yu, Zhi Zhou, Dongmei Hu, et al. Pathogenic Pseudorabies Virus, China, 2012 Emerging Infectious Diseases, No. 1, January 2014) (the applicant promises to open it to public for 20 year from the patent application date according to provisions of Guidelines for Patent Examination), HN1202 strain (deposited in the China Center for Type Culture Collection on Aug. 26, 2013, of which the accession number is CCTCC NO. V 201335 and the address is Wuhan University, Wuhan, China), according to methods in Example 1 and 2. The names of the attenuated strains obtained were NVDC-PRV-BJ with deletion of gI/gE/11K/28K/TK, NVDCPRV-HEB with deletion of gI/gE/11K/28K/TK, NVDC-PRV-SD with deletion of gI/gE/11K/28K/TK, and PRVHN1202 with deletion of gI/gE/11K/28K/TK. The deletion of genes was verified through comparison of PCR results with that of parent strains respectively.

Example 8

Preparation of Vaccine Compositions of the Attenuated Variant Strains of NVDC-PRV-BJ Strain, NVDC-PRV-HEB Strain and NVDC-PRV-SD Strain, HN1202 PRV Strain Each attenuated vaccine strains prepared in Example 7 was proliferated according to the method from Example 5.1, mixed with the protective agent (prepared by adding 40 g of sucrose and 8 g of gelatin into every 100 ml of deionized water, and autoclaved (under 121° C. for 30 min) after fully melted) at a volume ratio of 1:1 and the mixed vaccine compositions were freeze-dried. The batch numbers of NVDC-PRV-BJ strain with deletion of gI/gE/11K/28K/TK, NVDCPRV-HEB strain with deletion of gI/gE/11K/28K/ TK, NVDC-PRV-SD strain with deletion of gI/gE/11K/28K/ TK and PRV HN1201 strain with deletion of gI/gE/11K/ 28K/TK were Q01, Q02, Q03 and Q04, respectively.

Example 9

Pathogenicity Test of the Virus Strains Prepared in Example 7

Pathogenicity test was conducted according to the method in Example 4, in which the piglets were randomly divided into 5 groups, each with 5 piglets, inoculated with 1 ml ($10^{7.0}TCID_{50}$/ml) of NVDC-PRV-BJ strain with deletion of gI/gE/11K/28K/TK, NVDC-PRV-HEB strain with deletion of gI/gE/11K/28K/TK, NVDC-PRV-SD strain with deletion of gI/gE/11K/28K/TK, and PRV HN1202 strain with deletion of gI/gE/11K/28K/TK by intranasal instillation, respectively. The results showed that all the piglets were alive in each group, with normal body temperature and no clinical signs. It proved that the virulence of mutated PRV strain was reduced through deletion of gI/gE/11K/28K/TK genes.

Example 10

Immunogenicity Assay of the Vaccines Prepared in Example 8

Immunogenicity assay of the vaccines prepared in Example 8 was conducted according to the method and dose in Example 6, in the meanwhile the piglets in the vaccine control group were inoculated with the live PRV vaccine, HB-98 strain Batch No. 1308011-1 (purchased from China Animal Husbandry Industry Co., Ltd. Chengdu Medical Equipments Factory). The piglets were challenged with 1□$10^{7.0}$TCID$_{50}$/piglet of PRV HN1201 strain on day 28 after immunization. After challenge, the body temperature of piglets was determined daily, and in the meanwhile clinical signs and death status were observed (the results are shown in Table 6).

TABLE 6 clinical status and challenge status for piglets challenged after immunization with live PRV vaccines

| Group | Vaccines | clinical signs and death status | Rate of protection |
|---|---|---|---|
| Group IV | Q01 | Normal body temperature, normal appetite, no abnormal clinical signs, survived | 100% (5/5) |
| Group V | Q02 | Normal body temperature, normal appetite, no abnormal clinical signs, survived | 100% (5/5) |
| Group VI | Q03 | Normal body temperature, normal appetite, no abnormal clinical signs, survived | 100% (5/5) |
| Group VII | Q04 | Normal body temperature, normal appetite, no abnormal clinical signs, survived | 100% (5/5) |
| Vaccine control group | the live PRV vaccine, HB-98 strain Batch No. 1308011-1 | Body temperature of five piglets increased for 7-10 days, loss of appetite, one piglet died and four survived. | 80% (4/5) |
| Blank control group | DMEM medium | Body temperature of all piglets increased, depression in all piglets, partially or completely loss of appetite, significant clinical signs, two piglets died on day 4 after challenge, and all died within 5 days after challenge. | 0% (0/5) |

The result from Table 6 indicated that immunizing piglets with the PRV vaccines prepared in Example 8 can block virus infection (i.e. displaying clinical signs), and provide 100% (5/5) protection rate for piglets, while the vaccine control group can only provide 80% (4/5) protection rate for piglets, and all the piglets in the blank control group died by day 5 after challenge, therefore the PRV vaccines of the present invention can provide excellent protection. In addition, the piglets exhibited substantially no clinical signs, indicating excellent immune protection of the PRV vaccines relative to live vaccines in the prior art.

Example 11

Monitoring of gB Antibodies after Immunization with Different Strain Vaccines 15 piglets at the age of around 13 days which were negative for PRV antigens and PRV antibodies were randomly divided into 5 groups, each with 5 piglets. Groups 1-3 were injected with the vaccine prepared in Example 5, which is PRV HN1201 strain with deletion of gI/gE/11K/28K/TK, with Batch No. 20140502, the live PRV vaccine Bartha K-61strain, with Batch No. 66KR, purchased from HIPRA, Spain, and the live PRV vaccine, K-61, with Batch No. 195-B59B purchased from Boehringer Ingelheim (US) respectively. All the dose for immunization is 1 ml/piglet (for commercial vaccine, 1 piglet dosage/piglet, according to protocols; the PRV HN1201 with deletion of gI/gE/11K/28K/TK vaccine, $10^{6.0}$TCID$_{50}$/piglet). The blank control group was inoculated with 1 mL/piglet of DMEM medium. The blood of piglets was collected on day 8, 10, 12, 14 and 21 after immunization, and gB antibody was determined according to the protocol of gB ELISA antibody detection kit (purchased from Biochek, Batch No. FS5763, Expiry Date: 2015 Jan. 7) after the serum was separated. The detailed results of detection are shown in Table 7 below.

TABLE 7

Results of detection of gB antibodies of piglets after immunization.

| Group | No. of piglet | Before immunization OD405 nm | S/P | Day 8 after immunization OD405 nm | S/P | Day 10 after immunization OD405 nm | S/P |
|---|---|---|---|---|---|---|---|
| PRV HN1201 strain with deletion of gI/gE/11K/28K/TK vaccine with Batch No. 20140502 | 1# | 0.184 | 0.025 | 0.398 | 0.469 | 0.439 | 0.555 |
| | 2# | 0.170 | −0.004 | 0.369 | 0.409 | 0.453 | 0.584 |
| | 3# | 0.172 | 0.000 | 0.263 | 0.189 | 0.360 | 0.390 |
| | 4# | 0.181 | 0.019 | 0.320 | 0.307 | 0.494 | 0.669 |
| | 5# | 0.182 | 0.021 | 0.339 | 0.347 | 0.400 | 0.474 |
| Bartha K-61 | 6# | 0.177 | 0.010 | 0.223 | 0.106 | 0.243 | 0.147 |
| | 7# | 0.176 | 0.008 | 0.256 | 0.174 | 0.286 | 0.237 |
| | 8# | 0.167 | −0.010 | 0.224 | 0.108 | 0.246 | 0.154 |
| | 9# | 0.186 | 0.029 | 0.221 | 0.102 | 0.219 | 0.098 |
| | 10# | 0.175 | 0.006 | 0.242 | 0.145 | 0.277 | 0.218 |
| K-61 | 11# | 0.162 | −0.019 | 0.195 | 0.059 | 0.185 | 0.035 |
| | 12# | 0.16 | −0.023 | 0.174 | 0.009 | 0.192 | 0.052 |

TABLE 7-continued

Results of detection of gB antibodies of piglets after immunization.

|  | 13# | 0.167 | −0.007 | 0.182 | 0.028 | 0.218 | 0.113 |
|---|---|---|---|---|---|---|---|
|  | 14# | 0.16 | −0.023 | 0.199 | 0.068 | 0.201 | 0.073 |
|  | 15# | 0.17 | 0.000 | 0.219 | 0.115 | 0.225 | 0.129 |

| Group | No. of piglet | Day 12 after immunization | | Day 14 after immunization | | Day 21 after immunization | |
|---|---|---|---|---|---|---|---|
|  |  | OD405 nm | S/P | OD405 nm | S/P | OD405 nm | S/P |
| PRV HN1201 | 1# | 0.471 | 0.621 | 0.678 | 1.051 | 1.069 | 1.863 |
| strain with | 2# | 0.510 | 0.702 | 0.631 | 0.953 | 0.984 | 1.686 |
| deletion of | 3# | 0.453 | 0.584 | 0.496 | 0.673 | 0.619 | 0.928 |
| gI/gE/11K/28K/TK | 4# | 0.596 | 0.881 | 0.687 | 1.070 | 0.844 | 1.396 |
| vaccine, Batch | 5# | 0.602 | 0.893 | 0.547 | 0.779 | 0.690 | 1.076 |
| No. 20140502 |  |  |  |  |  |  |  |
| Bartha K-61 | 6# | 0.275 | 0.214 | 0.290 | 0.245 | 0.570 | 0.827 |
|  | 7# | 0.302 | 0.270 | 0.317 | 0.301 | 0.418 | 0.511 |
|  | 8# | 0.283 | 0.231 | 0.309 | 0.285 | 0.315 | 0.297 |
|  | 9# | 0.211 | 0.081 | 0.223 | 0.106 | 0.316 | 0.299 |
|  | 10# | 0.272 | 0.208 | 0.299 | 0.264 | 0.486 | 0.652 |
| K-61 | 11# | 0.239 | 0.162 | 0.274 | 0.244 | 0.314 | 0.338 |
|  | 12# | 0.205 | 0.082 | 0.211 | 0.096 | 0.277 | 0.251 |
|  | 13# | 0.248 | 0.183 | 0.25 | 0.188 | 0.449 | 0.655 |
|  | 14# | 0.256 | 0.202 | 0.285 | 0.27 | 0.321 | 0.354 |
|  | 15# | 0.28 | 0.258 | 0.3 | 0.305 | 0.385 | 0.505 |

Note:
evaluation criteria: negative, S/P value ≤ 0.499; positive, S/P value ≥ 0.500.

In conclusion, the antibody test results showed that, all gB antibodies turned positive on day 12 after immunization with PRV HN1201 strain with deletion of gI/gE/11K/28K/TK, while not all the gB antibodies had turned positive on day 21 after immunization with the two control vaccine. It showed that PRV HN1201 strain with deletion of gI/gE/11K/28K/TK could provide earlier immune protection.

Example 12

Monitoring of gE Antibodies after Immunization with Four Genes Deleted Strain Vaccine and Challenge.

15 piglets at the age of around 13 days which were negative for PRV antigens and PRV antibodies were randomly divided into 3 groups, each with 5 piglets. Groups 1-3 were injected with the vaccine prepared in Example 5, which is PRV HN1201 strain with deletion of gI/gE/11K/28K/TK, with Batch No. 20140502, the live PRV vaccine, Bartha K-61strain, with Batch No. 66KR, purchased from HIPRA, Spain, and the live PRV vaccine, K-61, with Batch No. 195-B59B purchased from Boehringer Ingelheim (US). All the dose for immunization is 1 ml/piglet (for commercial vaccine, 1 piglet dosage/piglet, according to protocols; the PRV HN1201 with deletion of gI/gE/11K/28K/TK vaccine, $10^{6.0}TCID_{50}$/piglet). The piglets were challenged with $10^{7.0}TCID_{50}$/piglet, 1 ml/piglet of PRV HN1201 strain on day 21 after immunization. The blood of piglets was collected daily continuously from day 7 to day 14 after challenge, and gE antibody was determined according to the protocol of gE ELISA antibody detection kit (purchased from IDEXX Co., Batch No. AK650, Expiry Date: 2015 Jun. 13) after the serum was separated. The results showed that gE antibody was still negative (If the value of S/N is less or equal to 0.60, the sample should be determined as PRV gE antibody positive) on Day 14 after challenge when the piglets were immunized with the vaccine prepared in Example 5, PRV HN1201 with deletion of gI/gE/11K/28K/TK with Batch No. 20140502, while gE antibody became positive at different level when the piglets were immunized with the two commercial vaccines. The detailed results of deletion are shown in Table 8 below.

TABLE 8

Results of detection of gE antibody of piglets after immunization.

| Group | No of piglet | Before challenge | | Day 7 after challenge | | Day 8 after challenge | | Day 9 after challenge | | Day b10 after challenge | |
|---|---|---|---|---|---|---|---|---|---|---|---|
|  |  | OD650 nm | S/N | OD650 nm | S/N | OD650 nm | S/N | OD650 nm | S/N | OD650 nm | S/N |
| PRV HN1201 | 1# | 1.024 | 1.041 | 0.917 | 0.932 | 0.956 | 0.972 | 0.860 | 0.874 | 0.863 | 0.877 |
| with deletion of | 2# | 1.006 | 1.008 | 0.979 | 0.980 | 0.931 | 0.932 | 0.889 | 0.890 | 0.780 | 0.781 |
| gI/gE/11K/28K/TK, | 3# | 1.070 | 1.072 | 0.990 | 0.991 | 1.007 | 1.009 | 0.970 | 0.971 | 0.929 | 0.930 |
| vaccine with | 4# | 1.052 | 1.054 | 0.795 | 0.796 | 0.899 | 0.872 | 0.972 | 0.943 | 1.000 | 0.970 |
| Batch No. | 5# | 0.969 | 0.970 | 0.912 | 0.913 | 0.915 | 0.916 | 0.922 | 0.923 | 0.683 | 0.684 |
| 20140502 |  |  |  |  |  |  |  |  |  |  |  |
| Bartha K-61 | 6# | 1.045 | 1.078 | 0.634 | 0.654 | 0.684 | 0.706 | 0.587 | 0.606 | 0.518 | 0.535 |
|  | 7# | 1.063 | 1.097 | 0.788 | 0.813 | 0.758 | 0.782 | 0.664 | 0.685 | 0.612 | 0.632 |
|  | 8# | 1.008 | 1.040 | 0.897 | 0.926 | 0.857 | 0.884 | 0.784 | 0.809 | 0.783 | 0.808 |
|  | 9# | 1.017 | 1.050 | 0.720 | 0.743 | 0.637 | 0.657 | 0.599 | 0.618 | 0.467 | 0.482 |
|  | 10# | 0.987 | 1.019 | 0.871 | 0.899 | 0.701 | 0.723 | 0.656 | 0.677 | 0.655 | 0.676 |

TABLE 8-continued

Results of detection of gE antibody of piglets after immunization.

| Group | No of piglet | | | | | | | | | |
|---|---|---|---|---|---|---|---|---|---|---|
| K-61 | 11# | 0.905 | 0.934 | 0.946 | 0.976 | 0.698 | 0.720 | 0.643 | 0.664 | 0.618 | 0.638 |
|  | 12# | 1.024 | 1.057 | 0.898 | 0.927 | 0.773 | 0.798 | 0.688 | 0.710 | 0.760 | 0.784 |
|  | 13# | 1.030 | 1.063 | 0.957 | 0.928 | 0.965 | 0.936 | 0.913 | 0.886 | 0.732 | 0.710 |
|  | 14# | 0.963 | 0.934 | 0.757 | 0.734 | 0.899 | 0.872 | 0.972 | 0.943 | 1.000 | 0.970 |
|  | 15# | 0.944 | 0.916 | 0.747 | 0.725 | 0.591 | 0.573 | 0.543 | 0.527 | 0.531 | 0.515 |

| Group | No of piglet | Day 11 after challenge | | Day 12 after challenge | | Day 13 after challenge | | Day 14 after challenge | |
|---|---|---|---|---|---|---|---|---|---|
|  |  | OD650 nm | S/N | OD650 nm | S/N | OD650 nm | S/N | OD650 nm | S/N |
| PRV HN1201 with deletion of gI/gE/11K/28K/TK vaccine, with Batch No. 20140502 | 1# | 0.884 | 0.898 | 0.877 | 0.891 | 0.871 | 0.885 | 0.880 | 0.894 |
|  | 2# | 0.854 | 0.855 | 0.780 | 0.781 | 0.793 | 0.794 | 0.732 | 0.733 |
|  | 3# | 0.907 | 0.908 | 0.905 | 0.906 | 0.904 | 0.905 | 1.067 | 1.069 |
|  | 4# | 0.965 | 0.936 | 0.864 | 0.838 | 0.997 | 0.967 | 0.929 | 0.901 |
|  | 5# | 0.623 | 0.624 | 0.718 | 0.719 | 0.784 | 0.785 | 0.718 | 0.719 |
| Bartha K-61 | 6# | 0.552 | 0.570 | 0.482 | 0.497 | 0.463 | 0.478 | 0.456 | 0.471 |
|  | 7# | 0.664 | 0.685 | 0.533 | 0.550 | 0.499 | 0.515 | 0.478 | 0.493 |
|  | 8# | 0.749 | 0.773 | 0.647 | 0.668 | 0.700 | 0.722 | 0.753 | 0.777 |
|  | 9# | 0.450 | 0.464 | 0.410 | 0.423 | 0.432 | 0.446 | 0.433 | 0.447 |
|  | 10# | 0.633 | 0.653 | 0.699 | 0.721 | 0.684 | 0.706 | 0.676 | 0.698 |
| K-61 | 11# | 0.568 | 0.586 | 0.472 | 0.487 | 0.472 | 0.487 | 0.449 | 0.463 |
|  | 12# | 0.745 | 0.769 | 0.659 | 0.680 | 0.659 | 0.680 | 0.714 | 0.737 |
|  | 13# | 0.785 | 0.761 | 0.678 | 0.658 | 0.505 | 0.490 | 0.425 | 0.412 |
|  | 14# | 0.965 | 0.936 | 0.864 | 0.838 | 0.997 | 0.967 | 0.929 | 0.901 |
|  | 15# | 0.578 | 0.561 | 0.528 | 0.512 | 0.457 | 0.443 | 0.398 | 0.386 |

The above results indicated that the vaccine strains in the present invention has a better immunogenicity than commercial vaccine in the prior art, and after immunization therewith a faster generation of the antibody can be achieved, and the effective amplification of virus in the body of pigs can be blocked, and gE antibody is negative.

Those are only preferred embodiments of the present invention as described above, which cannot be used to limit the present invention. Any change, substitution or modification etc., which are within the spirit and principle of the invention, should be included within the scope of protection of the present invention.

What is claimed is:

1. An attenuated strain of porcine pseudorabies virus comprising:
   inactivated proteins,
   wherein the inactivated proteins consist of inactivated gI, gE, 11K, and 28K proteins, and
   wherein the attenuated strain of porcine pseudorabies virus is an HN1201 strain, which is a variant strain of porcine pseudorabies virus.

2. The attenuated strain of porcine pseudorabies virus of claim 1, wherein the whole ORF of gI/gE/11K/28K gene is deleted from the attenuated strain of porcine pseudorabies virus.

3. The attenuated strain of porcine pseudorabies virus of claim 1, wherein the inactivated gE protein of the HN1201 strain is derived from a native gE sequence comprising the sequence of SEQ ID NO: 5 before inactivation.

4. The attenuated strain of porcine pseudorabies virus of claim 1, wherein the HN1201 strain is characterized by generating a display of clinical signs of infection selected from the group consisting of high fever, depression, and partial or complete loss of appetite in a pig previously immunized with a Bartha K-61 or a HB-98 strain of porcine pseudorabies virus.

5. The attenuated strain of claim 4, wherein the HN1201 strain is characterized by generating a display of clinical signs of infection selected from the group consisting of depression and loss of appetite in a piglet at the age of 9-10 days.

6. An attenuated strain of porcine pseudorabies virus comprising inactivated proteins, wherein the inactivated proteins consist of inactivated gI, gE, 11K, 28K, and TK proteins; and wherein the attenuated strain of porcine pseudorabies virus is an HN1201 strain, which is a variant strain of porcine pseudorabies virus.

7. The attenuated strain of porcine pseudorabies virus of claim 6, wherein at least a portion of the gene encoding TK protein is deleted to generate a second nucleotide sequence, wherein the second nucleotide sequence comprises SEQ ID NO: 4.

8. A vaccine composition, comprising:
   an immunizing amount of an antigen of an attenuated strain of porcine pseudorabies virus and a carrier,
   wherein the attenuated strain of porcine pseudorabies virus comprises inactivated proteins, and wherein the inactivated proteins consist of inactivated gI, gE, 11K, and 28K proteins, and
   wherein the attenuated strain of porcine pseudorabies virus comprises an HN1201 strain, which is a variant strain of porcine pseudorabies virus.

9. The vaccine composition of claim 8, wherein the immunizing amount comprises at least $10^{6.0}$ TCID$_{50}$/ml of the attenuated strain of porcine pseudorabies virus.

10. The vaccine composition of claim 8, wherein the antigen comprises a live attenuated strain of porcine pseudorabies virus, and wherein the vaccine composition further comprises a cryoprotectant.

11. The vaccine composition of claim 8, further comprising an inactivated pathogen or antigen.

12. The vaccine composition of claim 11, wherein the inactivated pathogen or antigen is selected from the group consisting classical swine fever virus, antigen of porcine reproductive and respiratory syndrome virus, antigen of porcine circovirus, antigen of haemophilus parasuis, and antigen of mycoplasma.

13. A method of treating and preventing pseudorabies infection, comprising immunizing a pig with the vaccine composition of claim 8.

* * * * *